United States Patent
Makino et al.

(10) Patent No.: US 7,983,872 B2
(45) Date of Patent: Jul. 19, 2011

(54) BODY MOVEMENT DETECTOR, BODY MOVEMENT DETECTION METHOD AND BODY MOVEMENT DETECTION PROGRAM

(75) Inventors: Kenichi Makino, Kanagawa (JP); Akane Sano, Tokyo (JP); Motoyuki Takai, Tokyo (JP)

(73) Assignee: Sony Corporation, Tokyo (JP)

( * ) Notice: Subject to any disclaimer, the term of this patent is extended or adjusted under 35 U.S.C. 154(b) by 271 days.

(21) Appl. No.: 12/279,557

(22) PCT Filed: Mar. 9, 2007

(86) PCT No.: PCT/JP2007/054710
§ 371 (c)(1),
(2), (4) Date: Aug. 15, 2008

(87) PCT Pub. No.: WO2007/105648
PCT Pub. Date: Sep. 20, 2007

(65) Prior Publication Data
US 2009/0240461 A1 Sep. 24, 2009

(30) Foreign Application Priority Data
Mar. 14, 2006 (JP) ................................ 2006-069343

(51) Int. Cl.
*G01P 15/00* (2006.01)
(52) U.S. Cl. ....................................................... 702/141
(58) Field of Classification Search .................. 702/141
See application file for complete search history.

(56) References Cited

U.S. PATENT DOCUMENTS
7,549,335 B2 * 6/2009 Inoue et al. ...................... 73/510
2008/0190201 A1  8/2008 Makino FOREIGN PATENT DOCUMENTS
| JP | 11 42220 | 2/1999 |
| JP | 2004 141669 | 5/2004 |
| JP | 2005 140533 | 6/2005 |
| JP | 2006 175206 | 7/2006 |
| JP | 2006 293861 | 10/2006 |

* cited by examiner

Primary Examiner — Drew A Dunn
Assistant Examiner — Stephen J Cherry
(74) Attorney, Agent, or Firm — Oblon, Spivak, McClelland, Maier & Neustadt, L.L.P.

(57) ABSTRACT

A vertical component is extracted from an acceleration vector corresponding to body movement of a user from a three-axis acceleration sensor, and the vertical-component is separated by a high-band/low-band separating unit into a high-band component and a low-band component. Using these components, a peak detection/determination processing unit detects a peak-position candidate of action of the user in the vertical direction, identifies a peak-position candidate on the basis of an energy ratio between the high-band component and the low-band component, performs waveform matching regarding a predetermined range including each peak-position candidate, thereby determining a peak position, and detects body movement on the basis of the peak position, and a step-position analyzing unit detects a body-movement pitch.

20 Claims, 17 Drawing Sheets

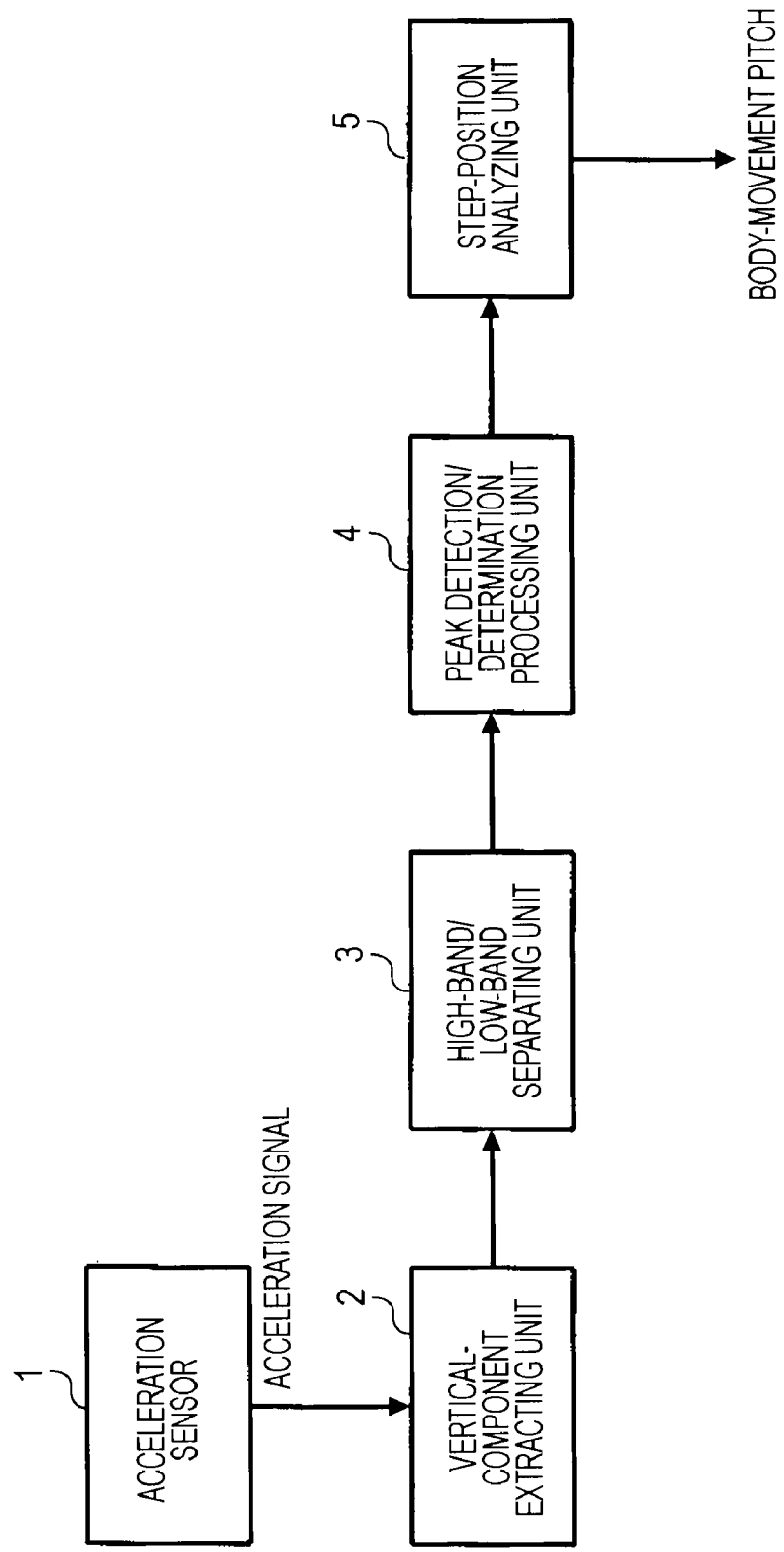

FIG. 2

$$a_n = \begin{pmatrix} a_{xn} \\ a_{yn} \\ a_{zn} \end{pmatrix} \quad \cdots (1\text{-}1)$$

$$g = \begin{pmatrix} g_x \\ g_y \\ g_z \end{pmatrix} \quad \cdots (1\text{-}2)$$

$$v_n = \frac{g^T a_n}{|g|} \quad \cdots (1\text{-}3)$$

FIG. 3

$$\theta = \tan^{-1} \frac{g_y}{g_x} \quad \cdots (2\text{-}1)$$

$$\phi = \tan^{-1} \frac{g_z}{\sqrt{(g_x)^2 + (g_y)^2}} \quad \cdots (2\text{-}2)$$

$$\begin{pmatrix} a'_{xn} \\ a'_{yn} \\ a'_{zn} \end{pmatrix} = \begin{pmatrix} \cos\phi & 0 & \sin\phi \\ 0 & 1 & 0 \\ -\sin\phi & 0 & \cos\phi \end{pmatrix} \begin{pmatrix} \cos\theta & \sin\theta & 0 \\ -\sin\theta & \cos\theta & 0 \\ 0 & 0 & 1 \end{pmatrix} a_n$$

$$\cdots (2\text{-}3)$$

FIG. 4

$$h_n = \sqrt{(a'y_n)^2 + (a'z_n)^2} \quad \cdots (3\text{-}1)$$

$$h_n = \sqrt{(ax_n)^2 + (ay_n)^2 - (v_n)^2} \quad \cdots (3\text{-}2)$$

FIG. 5

$$a_n = \begin{pmatrix} ax_n \\ ay_n \end{pmatrix} \cdots (4\text{-}1) \qquad g = \begin{pmatrix} gx \\ gy \end{pmatrix} \cdots (4\text{-}2)$$

$$\theta = \tan^{-1} \frac{gy}{gx} \quad \cdots (4\text{-}3)$$

$$\begin{pmatrix} a'x_n \\ a'y_n \end{pmatrix} = \begin{pmatrix} \cos\theta & \sin\theta \\ -\sin\theta & \cos\theta \end{pmatrix} a_n \quad \cdots (4\text{-}4)$$

FIG. 6
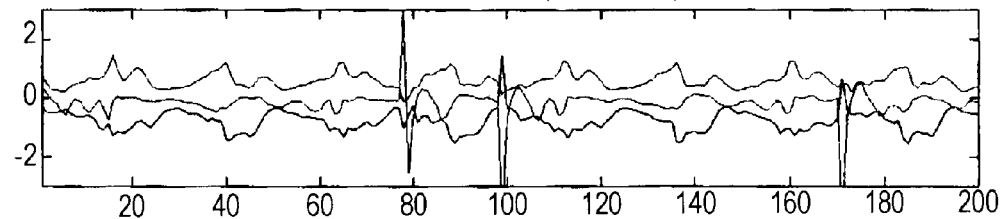
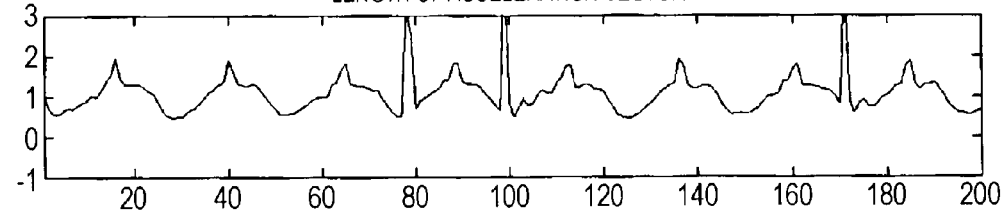
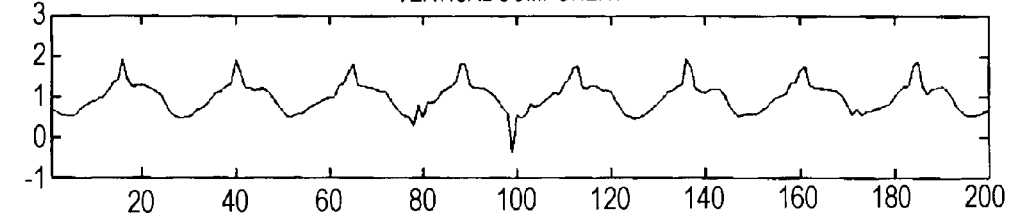
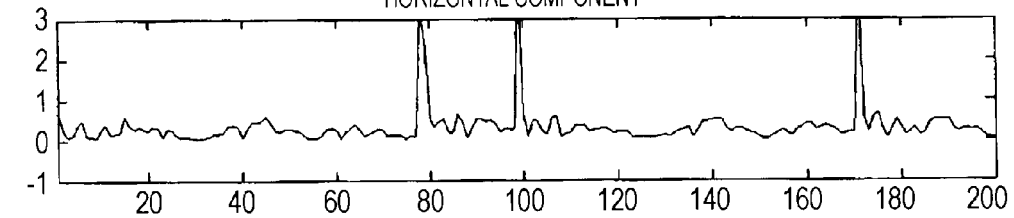

$$eh = \sum_{i=n1}^{n2} (xh(i))^2 \quad \cdots (5-1)$$

$$el = \sum_{i=n1}^{n2} (xl(i))^2 \quad \cdots (5-2)$$

$$d = \frac{eh}{el} \quad \cdots (5-3)$$

$$Ps = \frac{T1 + T2 + T3}{3} \qquad \cdots (6-1)$$

BODY MOVEMENT DETECTOR, BODY MOVEMENT DETECTION METHOD AND BODY MOVEMENT DETECTION PROGRAM

TECHNICAL FIELD

This invention relates to, for example, an apparatus, a method, and a program that detect and use body movement of a user, such as a pedometer.

BACKGROUND ART

For the purpose of self health management or the like, it is a common practice to grasp one's own amount of exercise using a pedometer. In many conventional pedometers, in order to count the number of steps accurately, because of their structures, restrictions exist regarding the mounting position or mounting direction of main units. In recent years, however, in order to further improve usability, body-movement detecting apparatuses in which it is possible to set a mounting position and mounting direction freely are proposed. Among them, a method and apparatus for performing posture estimation using a multi-axis acceleration sensor and performing body-movement detection using the same sensor have been proposed. This is advantageous in that implementation at an inexpensive cost is possible compared with a method of using an angle sensor or the like for posture estimation.

For example, Japanese Unexamined Patent Application Publication No. 2004-141669 discloses a method in which an acceleration is detected by a plurality of body-movement sensors having mutually different detecting directions, an operation axis is determined/selected by analyzing signal patterns of the individual sensors, and walking detection is performed by signal analysis of the operation axis. Furthermore, Japanese Unexamined Patent Application Publication No. 2005-140533 discloses a method in which an acceleration sensor having mutually orthogonal two axes or three axes is mounted, an exercise direction of body movement is estimated from a combined vector of sensor signals of individual axes, and body movement is detected by analyzing signal components in the estimated exercise direction.

DISCLOSURE OF INVENTION

However, according to the method disclosed in Japanese Unexamined Patent Application Publication No. 2004-141669, since only one sensor suitable for measurement is selected from a plurality of sensors as an operation axis, there are cases where the direction of user's body movement to be detected (exercise direction) of does not coincide with the selected operation axis, presumably, there exists a possibility that accurate measurement of the number of steps is prohibited by being affected by body movement other than walking. Furthermore, according to the method disclosed in Japanese Unexamined Patent Application Publication No. 2005-140533, since the nature of signal waveforms is not taken into consideration and only the signal intensity is considered as an issue, presumably, there exists a possibility that body movement other than walking is also counted.

Here, the body movement other than walking means actions other than actions that occur in the vertical direction on the body of the user in accordance with walking, and various actions are conceivable, such as an action in a case where a pedometer for measuring the number of steps of the user is held by a hand of the user and a swing in the horizontal direction occurs, a pendulum movement that occurs in a case where, for example, a pedometer for measuring the number of steps of the user is hung on the neck of the user by a hanging strap.

Thus, it is desired that only body movement of the user in the vertical direction during walking can be detected accurately and can be counted without being affected by body movement of the user other than walking, so that it is possible to measure the number of steps of the user accurately. Furthermore, considering body movement of the user in detail, the state is stationary in some cases, or there are also transient states from a walking state to a stationary state. Furthermore, different states exist even among action states, such as a walking state and a running state. Thus, if it is possible to accurately grasp the walking pitch of the user (walking rate or the number of steps (number of times) per unit time), it is possible to accurately grasp the action state of the user, which serves to measure the number of steps further accurately and so forth.

In view of the above, it is an object of this invention to make it possible to accurately detect body movement (action) of a user in the vertical direction without being affected by various types of noise, and to make it also possible to accurately detect and use a body-movement (action) pitch of the user as needed.

In order to solve the problems described above, a body-movement detecting apparatus of the invention according to Claim 1 is characterized by including an acceleration sensor configured to be mounted on a body of a user;

vertical-component extracting means for extracting a vertical component of an acceleration from a detection output from the acceleration sensor;

separating means for performing component separation of the vertical component extracted by the vertical-component extracting means into a high-band component and a low-band component;

detecting means for detecting a peak-position candidate on the basis of the low-band component of the vertical component separated by the separating means;

identifying means for identifying the peak-position candidate detected by the detecting means as a peak-position candidate in a case where a ratio between energy of the low-band component and energy of the high-band component in a predetermined range including the peak-position candidate is less than a predetermined value; and body-movement detecting means for detecting body movement of the user on the basis of the peak-position candidate identified by the identifying means.

According to the body-movement detecting apparatus of the invention according to Claim 1, a vertical component of body movement of a user is extracted by the vertical-component extracting means from a detection output from the acceleration sensor. The extracted vertical component is separated by the separating means into a high-band component and a low-band component. The low-band component obtained by separation includes components corresponding to body movement of the user, and it is used by the detecting means to detect a peak-position candidate of body movement.

Furthermore, for each predetermined range including each peak-position candidate detected, a ratio of energy of the high-band component to energy of the low-band component is obtained. Noise is likely to be mixed into the high-band component. Thus, in a case where the ratio of the energy of the high-band component to the energy of the low-band component is less than a predetermined value, the peak-position candidate in the predetermined range is identified as a peak position. Conversely, in a case where the ratio of the energy of the high-band component to the energy of the low-band component is greater than the predetermined value, the peak-position candidate in the predetermined range is excluded from peak-position candidates. On the basis of the peak-position candidates identified as above, body movement of the user is detected by the body-movement detecting means.

Accordingly, it becomes possible to precisely detect body movement of the user in the vertical direction without being affected by noise or the like.

Furthermore, a body-movement detecting apparatus of the invention according to Claim 2 of this application is the body-movement detecting apparatus according to Claim 1, characterized by including:

deciding means for defining a range of a comparison subject and comparing waveforms regarding a predetermined range including each peak-position candidate identified by the identifying means, and deciding the peak-position candidate as a peak position in a case where matching is achieved, wherein the body-movement detecting means detects body movement of the user on the basis of the peak position decided by the deciding means.

According to the body-movement detecting apparatus of the invention according to Claim 2, regarding a predetermined segment including each peak-position candidate identified by the identifying means, a segment that serves as a pair is defined and waveforms are compared, and the peak-position candidate of the reference of comparison is decided as a peak position in a case where waveforms in both segments coincide, and the peak-position candidate is excluded from peak positions in a case where the waveforms do not coincide.

Accordingly, a case where a peak accidentally occurs due to mixing of noise is excluded, and only a peak position truly corresponding to body movement of the user in the vertical direction is extracted and identified, so that it becomes possible to accurately detect body movement of the user.

Furthermore, a body-movement detecting apparatus of the invention according to Claim 3 is the body-movement detecting apparatus according to Claim 1 or 2, characterized by including interval estimating means for estimating a step interval by performing analysis regarding a time-series pattern formed of a plurality of peak-position candidates identified by the identifying means or a time-series pattern formed of a plurality of peak positions decided by the deciding means; and discriminating means for discriminating at least three states of "stationary", "walking/running", and "undefined" as action states of the user on the basis of the step interval estimated by the interval estimating means.

According to the body-movement detecting apparatus of the invention according to Claim 3, the interval estimating means estimates the step interval of the peak-position candidates identified by the identifying means (interval between the identified peak-position candidates) or the step interval of the peak positions decided by the deciding means (interval between the decided peak positions), and on the basis of the estimated step interval, the discriminating means discriminates whether the action state of the user is in the "stationary" state, the "walking/running" state, or the "undefined" state.

Accordingly, it becomes possible to accurately grasp the action state of the user and to control a device in accordance with the action state of the user, and it also becomes possible to accurately grasp the step interval in a case where the user is in the "walking/running" state.

Furthermore, a body-movement detecting apparatus of the invention according to Claim 11 is the body-movement detecting apparatus according to Claim 1, characterized in that:

the acceleration sensor is of a multi-axis type, and the vertical-component extracting means calculates a gravitational acceleration vector from an acceleration vector that is a detection output from the multi-axis acceleration sensor, and extracts a vertical component of an acceleration by performing calculation using the acceleration vector from the multi-axis acceleration sensor and the calculated gravitational acceleration vector.

According to the body-movement detecting apparatus of the invention according to Claim 11, the vertical-component extracting means calculates a gravitational acceleration vector from a detection output (acceleration vector) from the multi-axis acceleration sensor, and extracts a vertical component of an acceleration by performing calculation using the detection output from the multi-axis acceleration sensor and the calculated gravitational acceleration vector.

Accordingly, regardless of the manner of mounting of the multi-axis acceleration sensor on the body of the user, it becomes possible to logically and accurately extract a vertical component of a detection output (acceleration vector) thereof.

BRIEF DESCRIPTION OF DRAWINGS

FIG. 1 is a block diagram for explaining a basic configuration of a body-movement detecting apparatus of an embodiment.

FIG. 2 is a diagram for explaining an acceleration vector an, a gravitational acceleration vector g, and a vertical component vn of the acceleration vector an in a case where a three-axis acceleration sensor is used.

FIG. 3 is a diagram for explaining a case where the vertical component vn of the acceleration vector an is obtained in consideration of declination angles of the gravitational acceleration vector g in the case where the three-axis acceleration sensor is used.

FIG. 4 is a diagram for explaining a case where a horizontal component hn of the acceleration vector an is obtained in the case where the three-axis acceleration sensor is used.

FIG. 5 is a diagram for explaining an acceleration vector an, a gravitational acceleration vector g, and a vertical component vn of the acceleration vector an in a case where a two-axis acceleration sensor is used.

FIG. 6 is a diagram for explaining an example of graphs of acceleration data (A), length of acceleration vector (B), vertical component (C), and horizontal component (D).

BEST MODE FOR CARRYING OUT THE INVENTION

Figure 7:
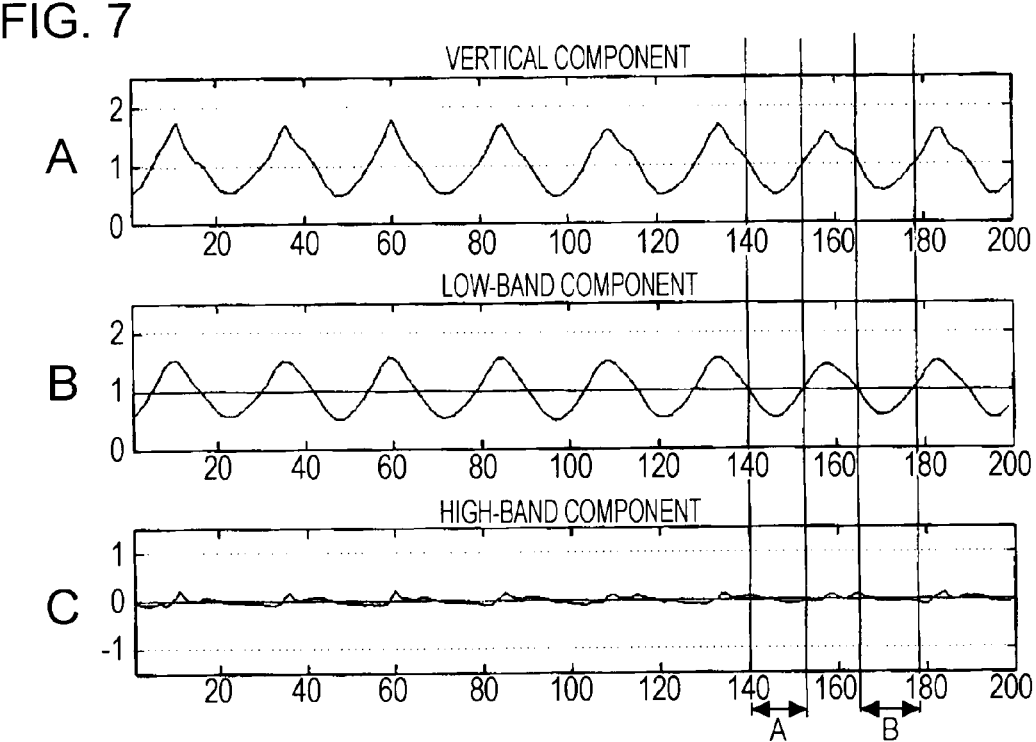
FIG. 7 is a diagram showing graphs of acceleration signals detected in a case where the body-movement detecting apparatus of the embodiment is used by being mounted on a waist part of a user.

Now, with reference to the drawings, an embodiment of an apparatus, a method, and a program according to this invention will be described.

[Regarding Basic Configuration of a Body-Movement Detecting Apparatus]

FIG. 1 is a block diagram for explaining a basic configuration of a body-movement detecting apparatus of this embodiment. As shown in FIG. 1, the body-movement detecting apparatus of this embodiment is formed of an acceleration sensor 1, a vertical-component extracting unit 2, a high-band/low-band separating unit 3, a peak detection/determination processing unit 4, and a step-position analyzing unit 5.

The body-movement detecting apparatus of this embodiment is used by being mounted on the body of a user. The acceleration sensor 1 detects an acceleration corresponding to body movement of the user at each constant timing, and supplies an output of this detection to the vertical-component extracting unit 2. From the detection output from the acceleration sensor 1, the vertical-component extracting unit 2 extracts a vertical component of an acceleration vector including a component corresponding to body movement in the vertical direction in a case where the user has performed an exercise such as walking or running, and supplies it to the high-band/low-band separating unit 3. Note that analog/digital (A/D) conversion of the acceleration vector detected by the acceleration sensor 1 may be performed on the side of the acceleration sensor 1, on the side of the vertical-component extracting unit 2, or between the acceleration sensor 1 and the vertical-component extracting unit 2.

The high-band/low-band separating unit 3 separates the vertical component of the acceleration vector from the vertical-component extracting unit 2 into a high-band component, in which noise is likely to be mixed, and a low-band component, which includes a component corresponding to body movement of the user in the vertical direction, and supplies each of these components to the peak detection/determination processing unit 4. The peak detection/determination processing unit 4 is a part that performs peak detection and body-movement detection based on detected peaks in response to supply of the high-band component and low-band component of the vertical component of the acceleration vector from the high-band/low-band separating unit.

That is, the peak detection/determination processing unit 4 detects a candidate of a peak position on the basis of the low-band component of the vertical component of the acceleration vector supplied from the high-band/low-band separating unit 3, and identifies the peak position as a candidate of a peak position of the vertical component in a case where the ratio of energy of the high-band component to energy of the low-band component in a predetermined range including the candidate of the peak position is less than a predetermined value.

The reason for using the ratio of the energy of the high-band component to the energy of the low-band component as above is that, as will be described later, noise is likely to be superposed on the high-band component and a peak that occurs due to mixing of noise is to be removed. On the basis of the peak-position candidate identified as above, it is possible to detect body movement of the user in the vertical direction with a relatively good precision. However, in order to detect body movement of the user in the vertical direction with even better precision, the peak detection/determination processing unit 4 of the body-movement detecting apparatus of this embodiment also performs a waveform matching process.

That is, for each identified peak-position candidate, the peak detection/determination processing unit 4 sets a predetermined range including the peak-position candidate, performs matching with a waveform in another predetermined range using a waveform in each predetermined range that is set as a subject, and determines the peak-position candidate included in the waveform of the comparison subject as a peak position in a case where matching is obtained. The reason for performing matching as above is that periodic exercise of the user, such as walking or running is to be detected reliably, and that if the waveforms of predetermined ranges including different peak-position candidates are similar, it becomes possible to determine that peak-position candidates are occurring periodically.

The peak position determined as above is absolutely a peak position that has occurred correspondingly to body movement of the user in the vertical direction, so that it becomes possible to detect body movement of the user in the vertical direction precisely according to the peak position determined. Furthermore, in the body-movement detecting apparatus of this embodiment, the step-position analyzing unit 5 is provided.

The step-position analyzing unit 5 is configured to receive provision of information indicating the peak position determined by the peak detection/determination processing unit 4 and analyze it so that a body-movement pitch of walking or running by the user (a tempo of walking or running) can be detected. Furthermore, as will be described later in detail, it is allowed to perform control in different manners in accordance with the detected body-movement pitch of the user.

Note that the term "pitch" means the rate or the number of times in a case where the same thing is repeated or something is performed at regular intervals. Thus, the term "body-movement pitch" means the rate or the number of times of body movement, and means the rate of walking (walking rate) or the number of steps per unit time when the body movement is walking.

Furthermore, in this specification, as a term synonymous with "pitch", in some cases, the term "tempo" is also used. The term "tempo" originally means a rate specified in a musical score for performance of a piece of music (a rate of progress of the piece of music). Thus, when a "playing tempo" of a piece of music is mentioned, it is a rate at a time of playing music data, and means the number of beats per minute (BPM: Beat Per Minutes).

Furthermore, when a "body-movement tempo (action tempo)" of the user is mentioned, it is a rate of body movement (action), and it means the number of units (one action (body movement)) of countable minimum action of the user per minute, for example, the number of steps per minute in a case where the body movement (action) of the user is walking or running, or the number of times of jumping per minute in a case where the action is jumping. As above, the term "pitch" and the term "tempo" used regarding body movement (action) of the user are used as substantially synonymous terms in this specification.

[Regarding Functions and Operations of Individual Parts of the Body-Movement Detecting Apparatus]

The functions and operations of individual parts constituting the body-movement detecting apparatus of this embodiment will be described below in more detail.

[Regarding the Acceleration Sensor 1]

First, the acceleration sensor 1 will be described. The body-movement detecting apparatus of this invention makes it possible to accurately detect body movement in the vertical direction corresponding to walking or running of the user on the basis of a detection output from the acceleration sensor 1 configured to be mounted on the body of the user. As the acceleration sensor 1, it is possible to use one-axis (single-axis) type, or multi-axis type such as two-axis type or three-axis type.

In a case where a one-axis acceleration sensor is used as the acceleration sensor 1, in order to enable detection of body movement of the user in the vertical direction, a certain degree of restriction is imposed regarding the mounting position and mounting direction. There exists a possibility that an effect in a direction other than the vertical direction is exerted depending on the mounting position, for example, in a case where a one-axis acceleration sensor is mounted on an arm, leg, or the like, it is conceivable that an effect of swinging of the arm or leg is exerted.

Thus, in the case where the one-axis acceleration sensor is used as the acceleration sensor 1, in order to detect as accurately as possible body movement in the vertical direction corresponding to walking or running of the user, for example, a restriction occurs that the one-axis acceleration sensor must be mounted on a waist part of the user so that the direction of detection of acceleration becomes the vertical direction. However, in a case where such restriction is observed, a detection output from the one-axis acceleration sensor can be used as a vertical component of acceleration. In this case, the one-axis acceleration sensor itself has the function as the vertical-component extracting unit 2.

In contrast, by using a two-axis or three-axis acceleration sensor constituted by mutually orthogonal axes as the acceleration sensor 1, it becomes possible to give flexibility to the mounting position and mounting direction of the acceleration sensor 1. However, in a case where a multi-axis acceleration sensor is used as the acceleration sensor 1, it becomes necessary to extract a vertical component from multi-axis detection outputs. In the body-movement detecting apparatus of this embodiment, for example, a three-axis acceleration sensor is used as the acceleration sensor 1. Thus, the vertical-component extracting unit 2 is provided at a subsequent stage of the acceleration sensor 1.

[Regarding the Vertical-Component Extracting Unit 2]

The vertical-component extracting unit 2 executes processing for (1) estimating, by using a detection output from the multi-axis acceleration sensor 1, a gravitational acceleration vector in a gravitational field thereof, and (2) on the basis of the result of the estimation of gravitational acceleration vector, extracting a signal component in the vertical direction from the same detection output of the acceleration sensor 1.

By extracting a vertical component by comprehensively using detection outputs regarding all the axes from the multi-axis acceleration sensor 1 as above, it is not necessary to estimate an operation axis, so that it becomes possible to accurately detect an exercise of the user in the vertical direction without being affected by the mounting position and mounting direction of the acceleration sensor 1 relative to the user.

Here, a case where a three-axis acceleration sensor is used as the acceleration sensor 1 will be described specifically. Suppose that the acceleration sensor 1 has three axes of an X axis, a Y axis, and a Z axis, and that an acceleration vector an at a certain time n, obtained from the acceleration sensor 1, is expressed by axn (X-axis component), ayn (Y-axis component), and azn (Z-axis component), as shown in equation (1-1) in FIG. 2. A gravitational acceleration vector g is estimated from the acceleration vector (data sequence of acceleration vector) an shown in equation (1-1) in FIG. 2, and body movement is also detected.

Specifically, regarding the estimation of the gravitational acceleration vector g, to be more simple, there exists a method in which moving average values of the individual axes of the acceleration vector an are calculated, and an average vector thereof is used as the gravitational acceleration vector g. In this case, in order to reduce effects of signal components attributable to body movement, it is desired that the calculation of moving averages be performed using a sufficiently long segment. Furthermore, a method may be used in which the gravitational acceleration vector g is calculated by analyzing the values of the individual axes of the acceleration vector an by using the least square method or the like.

Let the result of estimating the gravitational acceleration vector g by using the acceleration vector an be expressed by gx (X-axis component), gy (Y-axis component), and gz (Z-axis component), as shown in equation (1-2) in FIG. 2. In this case, the vertical component vn of the acceleration vector an can be obtained by calculation shown in equation (1-3) in FIG. 2. That is, as shown in equation (1-3) in FIG. 2, the vertical component vn of the acceleration vector an can be obtained by dividing the product of the inner product of the gravitational acceleration vector 9 and the acceleration vector an by the absolute value (magnitude) of the gravitational acceleration vector g.

As above, it is possible to obtain more accurately the vertical component vn by calculation from the acceleration vector an detected by the three-axis acceleration sensor 1 and the gravitational acceleration vector g obtained from the acceleration vector. That is, this invention is made on the basis of a conception that it is possible to accurately detect body movement of a user in the vertical direction by comprehensively using detection outputs from the three-axis acceleration sensor 1 and separating only a vertical component therefrom by numerical calculation.

Furthermore, similar calculation can also be performed by obtaining angles of declination of the gravitational acceleration vector g in a three-dimensional space and rotating the acceleration vector an. That is, when declination angles θ and φ regarding the gravitational acceleration vector g are as shown in (2-1) and (2-2) in FIG. 3, a'xn calculated by equation (2-3) in FIG. 3 is a vertical component of the acceleration vector an, and a'xn coincides with the vertical component vn. Furthermore, the inner product of the vector a'yn and the vector a'zn is the orthogonal projection of the acceleration vector an onto a plane for which the gravitational acceleration vector g is a normal vector.

That is, since it is possible to perform component separation of the acceleration vector an obtained by detection outputs from the three-axis acceleration sensor 1 into a vertical component and a horizontal component, it is also possible to detect body movement in the horizontal direction by analyzing the horizontal component as well as the vertical component. Specifically, the length hn of the horizontal vector can be obtained by equation (3-1) in FIG. 4 or equation (3-2) in FIG. 4.

In a case where a calculating equation is used in which declination angles of the gravitational acceleration vector are considered as above, it is possible to obtain relatively simply and also accurately body movement of the user in the vertical direction and in the horizontal direction.

Note that although description has been given here regarding a case where the three-axis acceleration sensor 1 is used as an example, there is no limitation thereto. The basic concept of this invention can be applied to a case where a two-axis acceleration sensor is used similarly to the case where a three-axis acceleration sensor is used.

That is, letting the acceleration vector an and the gravitational acceleration vector 9 detected by the two-axis acceleration sensor be expressed as equation (4-1) (acceleration vector) in FIG. 5 and equation (4-2) (gravitational acceleration vector) in FIG. 5, similarly to the case where a three-axis acceleration sensor is used, it is possible to calculate a vertical component according to equation (1-3) in FIG. 2.

Furthermore, letting the declination angle θ of the gravitational acceleration vector g be expressed as shown in equation (4-3) in FIG. 5, it is possible to perform component separation of the acceleration vector an into a vertical component a'xn thereof and a horizontal component a'yn perpendicular to it according to equation (4-4) in FIG. 5, and a'xn coincides with the vertical component vn.

As above, according to the equations shown in FIG. 5 and equation (1-3) shown in FIG. 2, even in the case where the two-axis acceleration sensor is used, it is possible to accurately detect body movement of the user in the vertical direction. Furthermore, in the case where the declination angle θ of the gravitational acceleration vector g is taken into consideration, it also becomes possible to accurately detect body movement of the user in the horizontal direction.

FIG. 6 shows, in the form of graphs, acceleration data obtained and data obtained in a case where the acceleration data is separated into components according to the basic concept of this invention described above in a case where acceleration data is obtained during four seconds at a sampling frequency of 50 Hz by a three-axis acceleration sensor configured to be mounted on a user while the user is performing an exercise such as walking. In FIG. 6, the horizontal axis is time (milliseconds), and the vertical axis is gravitational acceleration (G). Furthermore, also in FIG. 7, FIG. 8, FIG. 10, FIG. 12, and FIG. 14, which will be described later, the horizontal axis is time (milliseconds), and the vertical axis is gravitational acceleration (G).

That is, FIG. 6A is a graph of acceleration data from the three-axis acceleration sensor, FIG. 6B is a graph of the length (magnitude) of acceleration vector calculated from acceleration data of the three axes, and FIG. 6C is a graph of a vertical component obtained by calculation from the acceleration data of the three axes by the method described using FIGS. 2 to 4. Furthermore, FIG. 6D is a graph of a horizontal component obtained by calculation from the acceleration data of the three axes by the method described using FIGS. 2 to 4.

Furthermore, the graphs shown in FIG. 6 show a case where, at a time of detection of acceleration data, while the user is performing an exercise mainly in the vertical direction, an exercise in the horizontal direction occurs at an approximately 80th sample, an approximately 100th sample, and a 170th sample, and this exists as a noise component.

However, since the noise component exists in the horizontal component, by performing component separation of the acceleration data (acceleration vector) into the vertical component (FIG. 6C) and the horizontal component (FIG. 6D) according to the basic concept of this invention, it is possible to remove noise of the horizontal component from the vertical component, so that it is understood that body movement of the user in the vertical direction can be detected accurately. Obviously, since noise of the vertical component can be removed from the horizontal component, it is possible to accurately detect body movement of the user in the horizontal direction. That is, by the component separation, an effect of noise reduction is achieved.

Note that although the vertical component of the acceleration vector is extracted by calculation here, there is no limitation thereto. For example, the length (magnitude) of the acceleration vector of each axis may be obtained by calculation, and an acceleration vector with a longest length may be used as a vertical component of the acceleration vector best reflecting the body movement of the user, or a detection output (acceleration vector) of an axis estimated as best reflecting the body movement of the user may be used as a vertical component.

However, in the case where a vertical component is identified according to the length of an acceleration vector or an axis corresponding to a vertical component is estimated, there are cases where a certain degree of restriction is imposed on the mounting position and mounting direction of the multi-axis acceleration sensor 1 relative to the user. However, in the case where a vertical component of the acceleration vector is extracted by calculation, as described earlier, restrictions are not imposed regarding the mounting position or mounting direction of the multi-axis acceleration sensor 1 relative to the user, so that flexibility of mounting of the body-movement detecting apparatus relative to a user can be improved.

[Regarding the High-Band/Low-Band Separating Unit 3]

Next, the function and operation of the high-band/low-band separating unit 3 will be described. As described earlier, let the vertical component vn extracted by the vertical-component extracting unit 2 be denoted by a function x(n). The vertical component x(n) of the acceleration vector from the vertical-component extracting unit 2 is supplied to the high-band/low-band separating unit 3. The high-band/low-band separating unit 3 is configured to be, for example, an LPF (Low Pass Filter), and it performs band division of the vertical component x(n) of the acceleration vector to separate it into a high-band component xh(n) and a low-band component xl(n).

At this time, it is desired that the characteristics of the high-band/low-band separating unit 3 as an LPF be such that 2 Hz to 4 Hz, which includes main components of acceleration by walking or running, is a passband. Furthermore, it is desired that the vertical component x(n), the high-band component xh(n), and the low-band component xl(n) be in phase.

The reason for separating the vertical component x(n) into the high-band component xh(n) and the low-band component xl(n) as above is that, as described earlier, the low-band component xl(n) includes a large amount of components that change in accordance with body movement of the user in the vertical direction, and noise components are likely to be mixed into the high-band component xh(n). The high-band component xh(n) and the low-band component xl(n) separated by the high-band/low-band separating unit 3 as above are supplied to the peak detection/determination processing unit 4.

[Regarding Function and Operation of the Peak Detection/Determination Processing Unit 4]

As described earlier, the peak detection/determination processing unit 4 detects a peak-position candidate on the basis of the low-band component xl(n) of the vertical component x(n) of the acceleration vector, and identifies a peak-position candidate on the basis of a component ratio between energy of the low-band component and energy of the high-band component for each predetermined range using the peak-position candidate as a reference.

Figure 8:
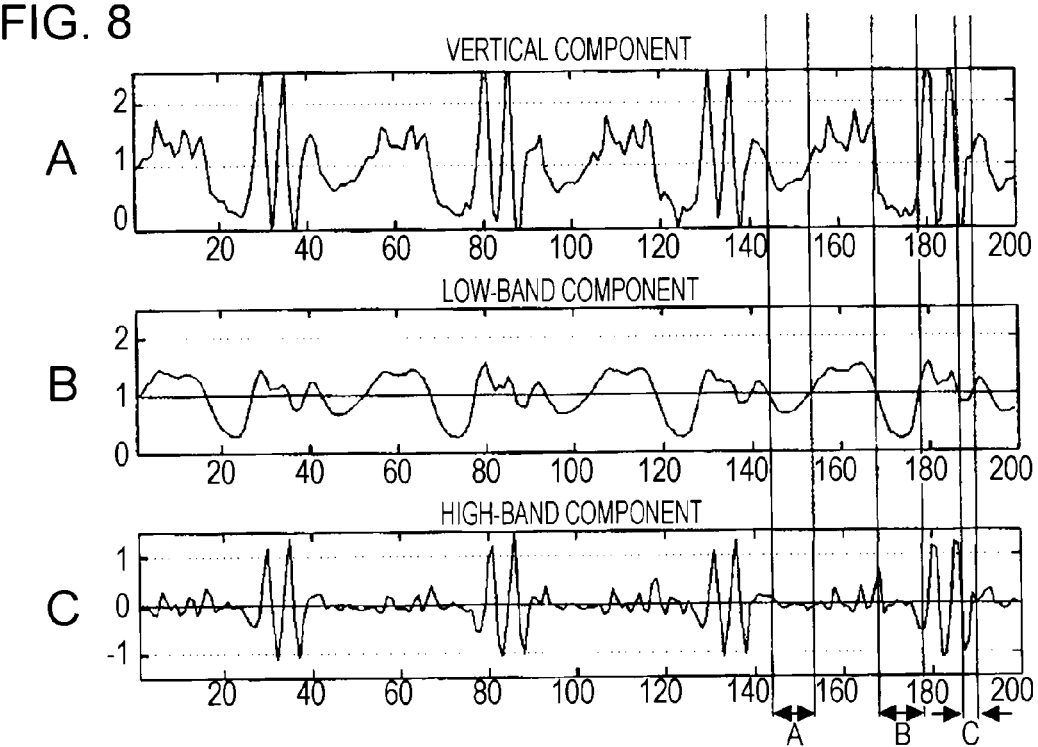
FIG. 8 is a diagram showing graphs of acceleration signals detected in a case where the body-movement detecting apparatus of the embodiment is used by being placed in a pocket of trousers of the user.

The reason for using the component ratio between the energy of the low-band component and the energy of the high-band component as above will be described. FIGS. 7 and 8 are diagrams showing graphs of acceleration signals in individual bands detected in cases where the body-movement detecting apparatus of this embodiment is mounted at different parts of the user. Specifically, FIG. 7 is a diagram showing a graph of acceleration signals detected in a case where the body-movement detecting apparatus of this embodiment is used by being fixed on a waist part of the user. FIG. 8 is a diagram showing a graph of acceleration signals detected in a case where the body-movement detecting apparatus of this embodiment is used by being placed in a pocket of trousers of the user.

In both FIGS. 7 and 8, acceleration signals detected by the three-axis acceleration sensor 1 while the user is walking are measured by sampling at 50 Hz. Furthermore, in both FIGS. 7 and 8, the graph on the uppermost row (FIG. 7A, FIG. 8A) is the vertical component extracted from the three-axis acceleration vector, i.e., x(n), the graph shown on the middle row (FIG. 7B, FIG. 8B) is the low-band component xl(n) in the vertical component x(n), and the graph on the lowermost row (FIG. 7C, FIG. 8C) is the high-band component xh(n) of the vertical component x(n).

Furthermore, as shown in FIG. 7, in a detection output of the three-axis acceleration sensor 1 in the case where the body-movement detecting apparatus of this embodiment is mounted at the waist part of the user, periodic changes are concentrated in the low-band component xl(n) shown on the middle row, and periodic changes are almost absent in the high-band component xh(n) shown on the lowermost row, so that it is understood that substantially only components corresponding to up and down movements attributable to walking are measured as acceleration signals.

Thus, in the case where the body-movement detecting apparatus of this embodiment is used by being mounted on the waist part of the user, it is possible to efficiently measure only components corresponding to body movement of the user in the vertical direction. Thus, it is possible to detect body movement such as walking or running by threshold checking or peak detection of the waveform of the low-band component xl(n) of the vertical component x(n), and by executing count processing on this, it is possible to implement a pedometer that is capable of counting the number of steps accurately.

Symmetrically to this, as shown in FIG. 8, in a detection output of the three-axis acceleration sensor 1 in the case where the body-movement detecting apparatus of this embodiment is used by being placed in a pocket of the user, vibration components (noise components), different from periodic up and down movements corresponding to walking, occur in both the low-band component xl(n) shown on the middle row and the high-band component xh(n) shown on the lowermost row, particularly, a large amount occurs in the high-band component xh(n) shown on the lowermost row. Thus, even if threshold checking or peak detection is performed regarding the low-band component, the possibility of incorrectly detecting a noise component, different from walking, as body movement is very high.

By the way, as shown in a segment A, a segment B, and a segment C in FIG. 8, in the graph of the low-band component shown on the middle row, in a case where a segment (region) where the amplitude is below 1 G is segmented, waveforms corresponding to up and down movements attributable to walking, which is a periodic exercise, are waveforms of the segment A and the segment B, and the waveform of the segment C is not periodic, and it is a vibration different from walking, i.e., a noise component. Furthermore, as shown in FIG. 8, as opposed to the segment A and the segment B, in which the high-band component is weak, in the segment C, the high-band component is strong.

As above, components corresponding to up and down movements of the user attributable to walking, which is a periodic exercise, appear prominently in the low-band component xl(n), and noise components appear prominently in the high-band component xh(n). Thus, for each peak-position candidate detected as a peak-position candidate, a predetermined region having a predetermined time width before and after the peak-position candidate is defined.

For example, the predetermined range can be defined as M sample segments before and M sample segments after the peak-position candidate (M is an integer greater than or equal to 1). Note that in FIGS. 7 and 8, a minimum value, which is relatively unsusceptible to the effect of noise, is detected as a peak value, and a peak position corresponding thereto is identified as a peak-position candidate.

Figures 9, 10:
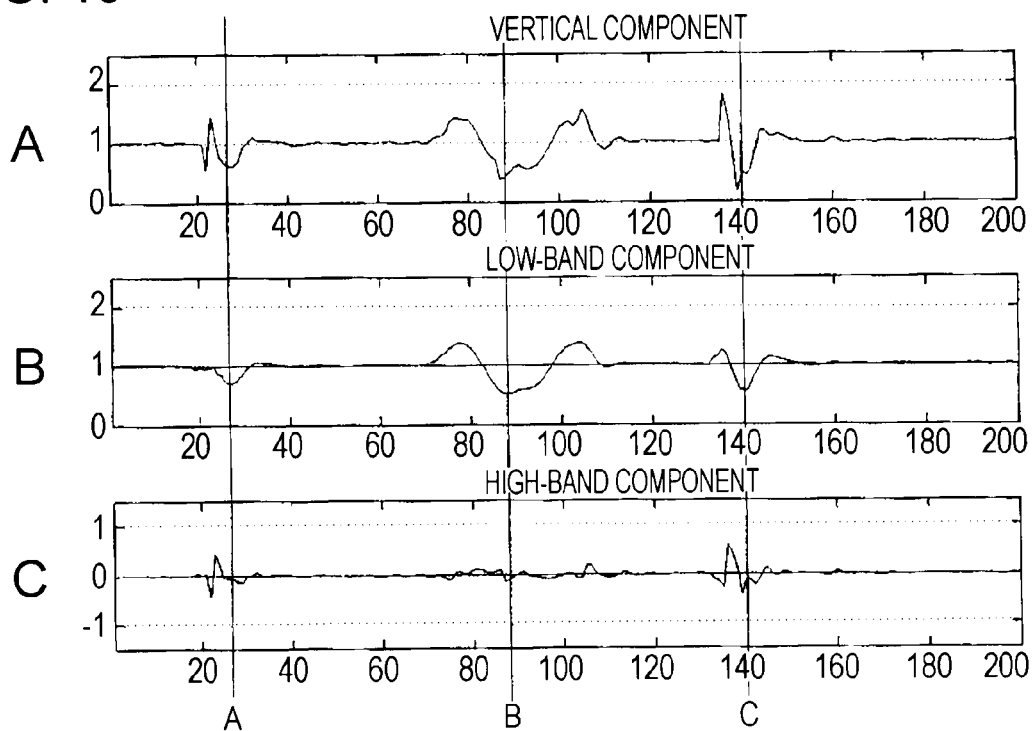
FIG. 9 is a diagram for explaining a calculating method for obtaining an energy ratio d.
FIG. 10 is a diagram showing graphs in a case where irregular signals are also mixed into a low-band component $xl(n)$ of a vertical component $x(n)$ of an acceleration vector detected by a multi-axis acceleration sensor 1.

In each predetermined range including a peak-position candidate, defined as above, a ratio d between energy of the low-band component xl(n) and energy of the high-band component xh(n) is obtained. FIG. 9 is a diagram for explaining a calculating method for obtaining the energy ratio d. The energy eh of the high-band component xh(n) of the vertical component x(n) of the acceleration vector can be obtained by equation (5-1) in FIG. 9. Furthermore, the energy el of the low-band component xl(n) of the vertical component x(n) of the acceleration vector can be obtained by equation (5-2) in FIG. 9.

Note that in equation (5-1) and equation (5-2) in FIG. 9, n1 denotes the start position of a predetermined region including a peak-position candidate, and n2 denotes the end position of the predetermined region including the peak-position candidate. Furthermore, the energy ratio d between the energy of the low-band component xl(n) and the energy of the high-band component xh(n) can be obtained by equation (5-3) in FIG. 9.

In a case where the energy ratio d obtained as above is less than a predetermined threshold D, the position detected as the peak-position candidate included in the predetermined region is identified as a peak-position candidate. That is, the position identified as the peak-position candidate is determined as forming a peak corresponding to an exercise of the user such as walking or running, and it is possible to accurately count the number of steps of the user who performed walking or running by counting the peak-position candidates. That is, by defining a certain threshold D and determining as walking or running only when the energy ratio d<the threshold D, the effect of vibration components, different from walking or running, can be excluded.

However, as described above, in order to detect changes corresponding to body movement of the user, such as walking or running, even if a peak-position candidate is detected on the basis of the low-band component $xl(n)$ of the vertical component $x(n)$ of the acceleration vector and a peak-position candidate is identified in consideration of the energy ratio d between the energy el of the low-band component $xl(n)$ and the energy eh of the high-band component $xh(n)$, still, presumably, there are cases where incorrect determination occurs.

FIG. 10 is a diagram showing graphs (irregular waveforms) in a case where irregular signals are also mixed into the low-band component $xl(n)$ of the vertical component $x(n)$ detected by the multi-axis acceleration sensor 1 due to the effect other than periodic body movement of the user, such as walking or running. In the case where an irregular operation, different from walking or running, occurs, for example, falling, dropping of the body-movement detecting apparatus, or jumping of the user, as represented in the graph of the low-band component $xl(n)$ on the middle row of FIG. 10, there are cases where components of the irregular body movement, different from walking or running, are mixed.

In the case where components of irregular body movement different from walking or running are mixed into the low-band component $xl(n)$ of the vertical component $x(n)$ of the acceleration vector as above, presumably, there are cases where it is incorrectly determined as body movement corresponding to walking or running, which is a periodic exercise. Thus, comparison as to whether signal waveforms are similar in certain segments is performed, and it is determined as walking or running if the waveforms are similar.

For example, in FIG. 10, which is graphs of an example of the vertical component $x(n)$ (FIG. 10A), the low-band component $xl(n)$ (FIG. 10B), and the high-band component $xh(n)$ (FIG. 10C) of the acceleration vector in a case where an irregular action different from walking or running occurs, it is possible to detect a position A, a position B, and a position C as peak positions. Regarding these positions, pairs are formed between the position A and the position B, the position B and the position C, and the position A and the position C, and matching is obtained regarding the waveforms around the individual peak positions between the pair.

In this case, as is apparent from FIG. 10, regarding the waveform in the vicinity of the position A, the waveform in the vicinity of the position B, and the waveform in the vicinity of the position C, there are no mutually similar pairs, so that it is determined as being different from body movement of walking or running, which is a periodic body movement, and it is possible to determine as not being body movement at a time of walking or running.

In contrast, as shown in FIGS. 7 and 8, in the case where the vertical component $x(n)$, the low-band component $xl(n)$, and the high-band component $xh(n)$ of the acceleration vector are detected, in a case where a predetermined segment including a position identified as a peak-position candidate is set, and a matching process with waveforms in one or more preceding or succeeding predetermined periods is executed, a position identified as a peak-position candidate since a similar case exists can be determined as a formal peak position.

Specifically, in the case of the example shown in FIG. 7, in order to reduce the effect of noise, by causing a minimum value to be taken as a peak value in the graph of the low-band component $xl(n)$, since the degree of similarity between the waveforms including adjacent peak positions is very high, it is possible to determine a position identified as each peak-position candidate as a peak position. Furthermore, also in the case of the example shown in FIG. 8, in order to reduce the effect of noise, a minimum value is caused to be taken as a peak value in the graph of the low-band component $xl(n)$. Thus, the degree of similarity between waveforms including the every other peak positions among peak-position candidates is very high, so that a position identified as each peak-position candidate can be determined as a peak position.

As above, a peak-position candidate is identified, another predetermined segment with which comparison is performed (matching is obtained) regarding a waveform in a predetermined segment including the candidate is defined, and in a case where the waveforms in both predetermined periods are compared with each other and the degree of similarity is high, the peak-position candidate included in the predetermined segment of the comparison subject can be determined as a peak position.

Another predetermined segment that is compared may be defined as appropriate, for example, between adjacent predetermined segments, between predetermined segments with one segment therebetween, or between predetermined segments with two segments therebetween. Alternatively, it is possible to arbitrarily set the positions or number of predetermined segments that are compared, such as performing comparison with one or more preceding predetermined segments (in the past direction) and determining the peak-position candidate in the predetermined segment of the reference of comparison as a peak position in a case where the degree of similarity with two or more predetermined segments is high.

As above, in the body-movement detecting apparatus of this embodiment, the peak detection/determination processing unit 4 not only detects a peak-position candidate from information (waveform) of the low-band component $xl(n)$ of the vertical component $x(n)$ of the acceleration vector and identifies a peak-position candidate in consideration of the energy ratio d between the energy el of the low-band component and the energy eh of the high-band component, but also performs waveform comparison (waveform matching) between predetermined segments including peak-position candidates, so that it becomes possible to accurately detect periodic body movement of the user, such as walking or running.

Furthermore, since it is possible to accurately detect periodic body movement of the user, such as walking or running, by counting body movement of the user, it is possible to implement a pedometer that is capable of accurately counting the number of steps of the user at a time of walking or running. Note that, if the precision may be degraded slightly, as described earlier, the number of steps may be counted according to peak-position candidates identified using the energy ratio d without performing waveform matching.

[Function and Operation of the Step-Position Analyzing Unit 5]

By the functions of the individual parts of the acceleration sensor 1, the vertical-component extracting unit 2, the high-band/low-band separating unit 3, and the peak detection/determination processing unit 4 described above, on the basis of detection outputs from the acceleration sensor 1 mounted on the body of the user, it is possible to accurately detect body movement in the vertical direction, which occurs on the body of the user correspondingly to walking or running by the user. By counting the body movement detected as above, it also becomes possible to accurately count the number of steps of the user.

However, the action state of the user is not always an action state in which walking or running is being performed, and in some cases, the state is a stationary state, or an undefined state that is neither a stationary state or an action state. Thus, if it is possible to accurately grasp the action state of the user, in a case where body movement is counted, such as counting the number of steps, it is possible to further prevent an incorrect operation such as counting body movement even in a stationary state or an undefined state.

Furthermore, if it is understood that the user is in an action state where an exercise such as walking or running is being performed, it becomes possible to accurately detect body movement of the user during the period, accurately grasp the body-movement pitch (body-movement tempo) of the user, and control a device in accordance with the transitive pitch of the user. Thus, in the body-movement detecting apparatus of this embodiment, the step-position analyzing unit 5 is configured to be capable of receiving supply of information indicating a peak position determined by the peak detection/determination processing unit 4, and based on this, accurately grasping the action state of the user, and also to be capable of accurately detecting the body-movement pitch in a case where the user is performing a periodic exercise, such as walking or running.

Figure 11:
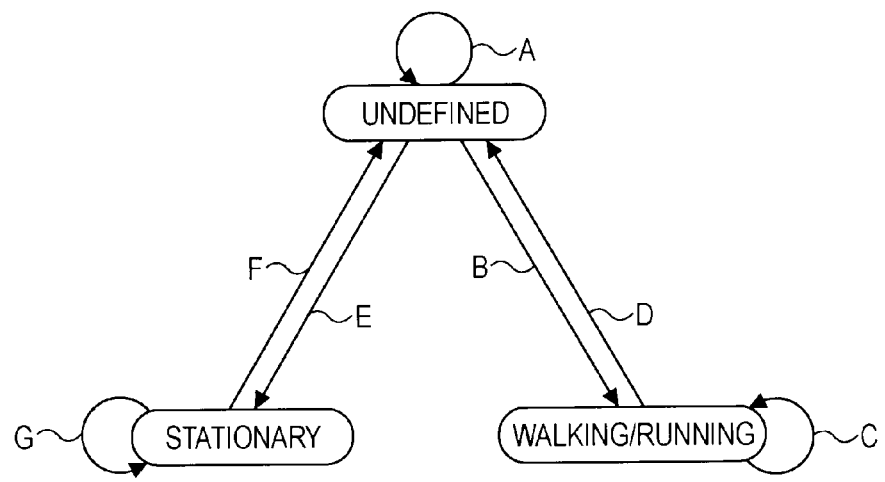
FIG. 11 is a diagram for explaining transition of action states of the user.

FIG. 11 is a diagram for explaining transition of the action state of the user. As shown in FIG. 11, it is assumed that three states of "undefined", "stationary", and "walking/running" exist as action states of the user. Here, "stationary" means a state where movement of the body of the user is completely absent, "walking/running" means a state where the user is walking or running, and "undefined" means a state other than the above two states. Furthermore, it is assumed that an initial state starts from "undefined". Furthermore, it is assumed that, in the case of a transition from the "stationary" state to the "walking/running" state or in the case of a transition from the "walking/running" state to the "stationary" state, the transition occurs via the "undefined" state.

Furthermore, in the step-position analyzing unit 5, on the basis of determined peak position information from the peak detection/determination processing unit 4, first, the action state of the user is determined. Here, in FIG. 11, by discriminating the individual transition states of transition A to transition G, the action state of the user is discriminated.

That is, transitions of action state are grasped in detail by also considering a case where each state is maintained as one transition state, such as a case where the "undefined" state is maintained is a transition A, a case where a change from the "undefined" state to the "walking/running" state occurs is a transition B, a case where the "walking/running" state is maintained is a transition C, a case where a transition from the "walking/running" state to the "undefined" state occurs is a transition D, a case where a transition from the "undefined" state to the "stationary" state occurs is a transition E, a case where a transition from the "stationary" state to the "undefined" state occurs is a transition F, and a case where the "stationary" state is maintained is a transition G.

Next, conditions for discrimination of the individual transition states will be described. As described earlier, the discrimination of the individual transition states is performed on the basis of a peak position determined by the peak detection/determination processing unit 4. Hereinafter, the "determined peak position" is also referred to as a "detected step". That is, the peak position determined by the peak detection/determination processing unit 4 is regarded as a step corresponding to a body movement of the user in the vertical direction. Furthermore, (1) if neither the condition for the case of the transition B or the condition for the case of the transition C, described below, is satisfied, the state is determined as the transition A, and the "undefined" state is maintained.

Furthermore, (2) after it is determined that the state is the transition A, regarding newest ones of detected steps (determined peak positions), time intervals between adjacent steps are calculated. In a case where the time intervals are constant, it is determined that the state is the transition B, in which a transition from the "undefined" state to the "walking/running" state occurs, and that the action state of the user has become the "walking/running" state. In this case, a reference step interval (reference pitch Ps) is calculated in advance. As will be described later, the reference step interval is an average value of intervals between steps used to determine that the state is the transition B.

Furthermore, (3) after it is determined that the state is the transition B or the transition C, in a case where the interval between a newly detected step and an immediately preceding step is within a certain error range relative to an integer multiple of the reference step interval (reference pitch Ps), the state is determined as the transition C, and the "walking/running" state is maintained. On the other hand, after the state is determined as the transition B or the transition C, in a case where the condition for determining the state as (3) the transition C described above is not satisfied, it is determined that the state is the transition D and that the action state of the user is the "undefined" state.

Furthermore, (5) after the state is determined as the transition A or the transition D, in a case where no step is detected (no peak position is determined) for a predetermined period or longer, it is determined that the state is the transition E, in which a transition from "undefined" to "stationary" occurs, and that the action state of the user is the "stationary" state. Furthermore, (6) after it is determined that the state is the transition E or the transition G, in a case where a step is detected (a peak position is determined), it is determined that the state is the transition F, in which a transition from "stationary" to "undefined" occurs, and that the action state of the user has become the "undefined" state.

On the other hand, (7) after the state is determined as the transition E or the transition G, in a case where no step is detected (no peak position is determined), the state is determined as the transition G, and as the action state of the user. The "stationary" state is maintained.

Note that in the determination of (2) whether the state is the transition B described earlier, the criterion for determining whether the step interval is constant may be determined according to whether a variance or standard deviation of step intervals exists, or according to whether the difference between the largest value and the smallest value is less than or equal to a threshold. Furthermore, as the reference step interval, an average of time intervals of steps used for determination may be used as described earlier. Alternatively, a mean value of time intervals of steps used for determination may be used.

Figure 12:
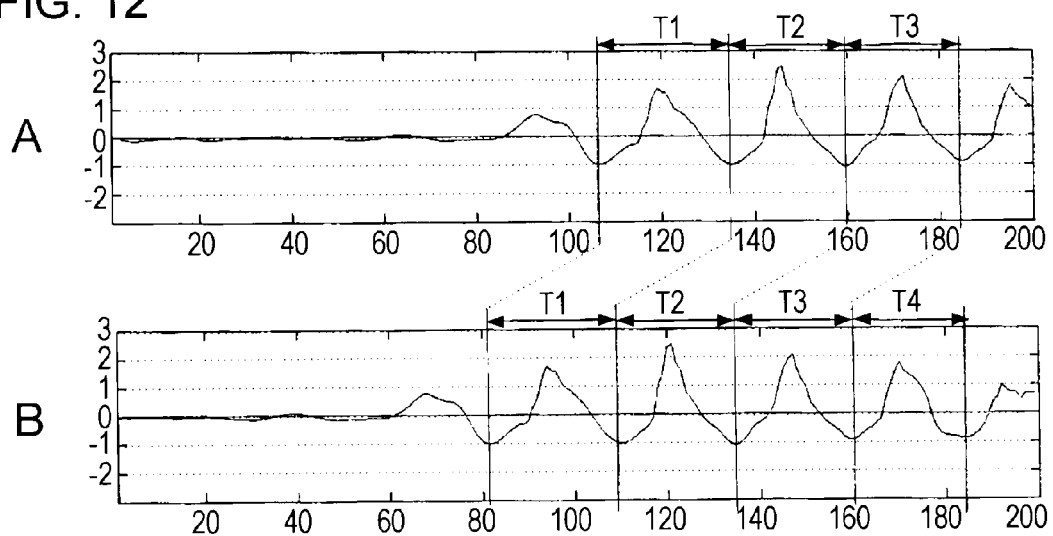
FIG. 12 is a diagram showing a waveform in a case where a step is detected (a peak position is determined) from a detection output of the acceleration sensor 1 in the body-movement detecting apparatus shown in FIG. 1.

FIG. 12 is a diagram showing waveforms in a case where a step is detected (a peak position is determined) from detection outputs of the acceleration sensor 1 using the functions of individual parts of the acceleration sensor 1, the vertical-component extracting unit 2, the high-band/low-band separating unit 3, and the peak detection/determination processing unit 4 of the body-movement detecting apparatus shown in FIG. 1. Also in FIG. 12, a peak is taken on the minimum-value side. The waveform shown in FIG. 12A represents the waveform in a case where four steps (determined peak positions) are detected from the "undefined" state. FIG. 12B represents a waveform in a case where an immediately succeeding step is detected from the state of FIG. 12A. Using such FIG. 12, an example of state transition will be described specifically.

First, suppose that the state is initially "undefined" in the waveform shown in FIG. 12A. Then, since four steps are detected (two peak positions are determined), the step-position analyzing unit 5 calculates individual step intervals of adjacent step segments T1, T2, and T3, and compares these step intervals. In the case of this example, since the intervals of the individual step segments T1, T2, and T3 are substantially constant, in this case, the state can be determined as the transition B, in which a transition from "undefined" to "walking/running" occurs.

Figures 13, 14:
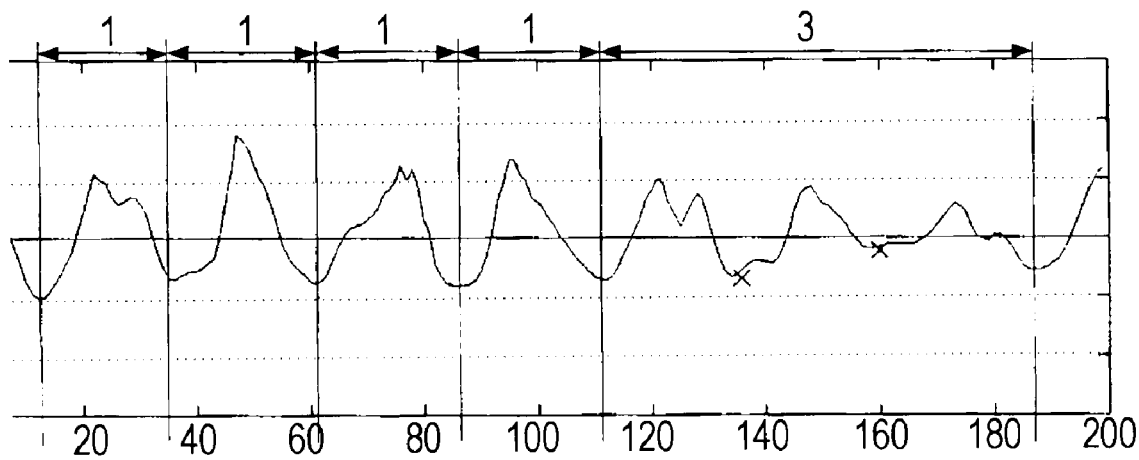
FIG. 13 is a diagram for explaining an example of an equation for calculating a reference pitch Ps.
FIG. 14 is a diagram for explaining an example of a case where a detecting miss of a peak position occurs in a "walking/running" state.

At this time, the step-position analyzing unit 5 calculates the reference pitch (reference step interval) Ps by equation (6-1) shown in FIG. 13. Note that equation (6-1) shown in FIG. 13 is an equation for calculating the reference pitch Ps in the state of FIG. 12A, and if the step segments increase, the segments added in the numerator and the number of segments in the denominator change.

Then, in a case where a change occurs from the state shown in FIG. 12A to the state shown in FIG. 12B, the step interval of the most recent step segment T4 is compared with the reference pitch Ps calculated by equation (6-1) in FIG. 13. In this case, since the step interval of the step segment T4 and the reference pitch Ps are substantially the same, it is determined that the difference is within the error range, the state is determined as the transition C, and the state of "walking/running" is maintained.

Note that as the period (step interval) of pitch during walking or running in the "walking/running" state, the reference pitch may be used as a representative value, or an average value of step intervals within a certain time segment or an average value of a predetermined number of step intervals may be used.

Furthermore, in the above description, without distinction between the "walking" state and the "running" state, the state is grasped as one state of the "walking/running" state. However, there is no limitation thereto. It may be allowed to grasp the "walking" state and the "running" state individually as different states.

As a criteria for distinction between walking and running, in addition to the condition for determination of the transition B of (2) described earlier, it is possible to (A) determine the state as the "running" state in a case where the step interval is less than a certain value and to determine the state as "walking" in other cases, or (B) determine the state as the "running" state in a case where the peak value of the waveform of acceleration is greater than or equal to a certain value and to determine the state as the "walking" state in other cases. Obviously, either the condition (A) or (B) described above may be used as described above, or both the conditions (A) and (B) described above may be used.

Furthermore, although the "walking" state and the "running" state may be defined as entirely different action states as described above, assuming that the state transition occurs according to FIG. 11, as an attribute of the "walking/running" state, using either one or both of the conditions (criteria) (A) and (B) described above, "walking" and "running" may be grasped separately.

Furthermore, regarding the determination as to whether the state is the transition C, instead of directly comparing the step interval and the reference pitch (reference step interval) Ps, determination is performed using an integer multiple of the reference pitch Ps as a reference. Doing as above serves to prevent unintended state transition in a case where a miss is step detection occurs.

For example, in the body-movement detecting apparatus of this embodiment, as described earlier, in the peak detection/determination processing unit 4, a peak-position candidate is detected, a peak-position candidate is identified in consideration of energy of the high band and the low band, and furthermore, waveform comparison is performed for each predetermined interval including the peak-position candidate, thereby determining a peak position.

However, there is a possibility that matching with nearby waveforms is not obtained and a detection miss occurs if the waveform of acceleration is temporarily disturbed even though the user is continuing walking. Thus, as described earlier, in a case where determination of the transition C is performed by the step-position analyzing unit 5, by "determining with reference to an integer multiple of the reference pitch", in the peak detection/determination processing unit 4 at the previous stage, it becomes possible to perform state estimation stably even if a detection miss of a walking step (a determination miss of a peak position) occurs.

For example, FIG. 14 shows an example of a case where, in the "walking/running" state, detection miss (count miss) of two steps (peak positions) indicated by × signs (cross signs) occurs, so that the interval between the step (peak position) detected most recently and the step (peak position) detected immediately before corresponds to three steps.

In the case of the example shown in FIG. 14, in the condition for determining whether the state is the transition C, in a case where the interval between the newly detected step and the immediately preceding step is within a certain error range relative to an integer multiple of the reference step interval (reference pitch Ps), the state is determined as the transition C, and the state of "walking/running" is maintained.

Thus, instead of simply accumulating detected steps one by one, even in a case where no step (peak position) is detected, in a case where the "walking/running" state is maintained, by using multiples of the reference pitch as subjects of accumulation, it becomes possible to measure the number of steps more accurately. Therefore, by applying this invention to a pedometer, it also serves to improve the accuracy of the pedometer.

As above, in the body-movement detecting apparatus of this embodiment, the individual parts of the acceleration sensor 1, the vertical-component extracting unit 2, the high-band/low-band separating unit 3, the peak detection/determination processing unit 4, and the step-position analyzing unit 5 function in an organized manner, so that it is possible to accurately detect body movement of the user, such as walking or running, and to grasp it.

[Application to Specific Apparatus]

Next, cases of application of an apparatus, method, and program to specific apparatuses will be described. Hereinafter, description will be given separately for a case of application of this invention to a pedometer, and a case of application to an acoustic playing apparatus.

[Regarding Application to a Pedometer]

Figure 15:
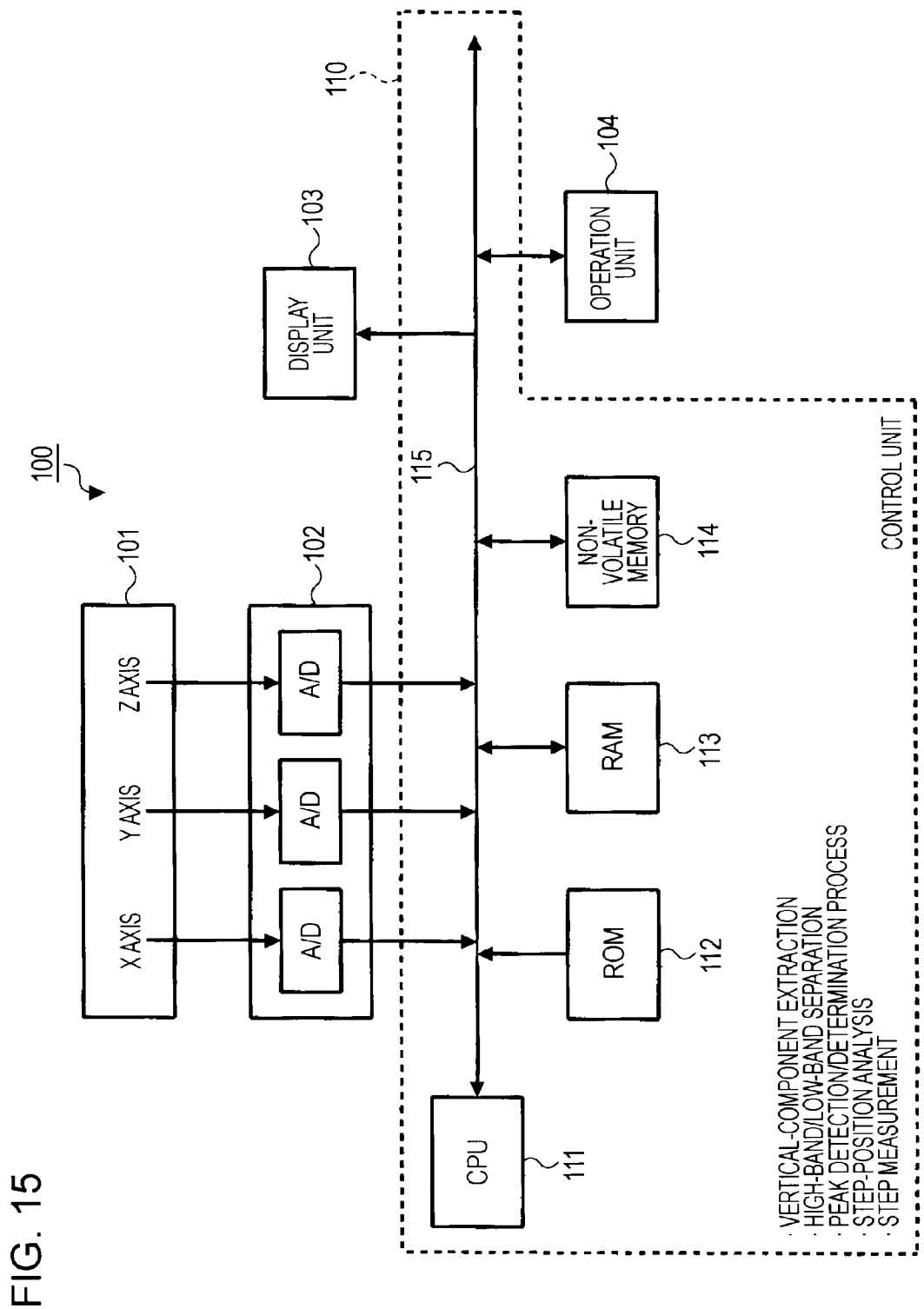
FIG. 15 is a block diagram for explaining a pedometer to which an embodiment of this invention is applied.

First, a case where an embodiment of an apparatus, method, and program of this invention is applied to a pedometer will be described. FIG. 15 is a block diagram for explaining a pedometer 100 of this embodiment. As shown in FIG. 15, the pedometer 100 of this embodiment is formed by connecting a three-axis acceleration sensor 101 to a control unit 110 via an A/D converter 102 and connecting a display unit 103 and an operation unit 104.

As the three-axis acceleration sensor 101, either one formed by arranging one-axis acceleration sensors on three axes of an X axis, a Y axis, and a Z axis orthogonal to each other, or one formed by encapsulating acceleration sensors of orthogonal three axes in one package may be used. The individual detection outputs (analog outputs) of the X axis, Y axis, and Z axis from the three-axis acceleration sensor 101 are supplied to the A/D converter 102, where they are converted into digital data in a format in which processing by the control unit 110 is allowed, and the digital data is supplied to the control unit 110.

The control unit 110 controls individual parts of the pedometer 100 of this embodiment, and, as shown in FIG. 15, it is configured as a microcomputer in which a CPU (Central Processing Unit) 111, a ROM (Read Only Memory) 112, a RAM (Random Access Memory) 113, and a non-volatile memory 114 are connected via a CPU bus 115.

Here, the CPU 111 executes various programs to form control signals supplied to individual parts, to perform various types of calculation, and so forth, and it serves as a main unit for processing or control in the control unit 110. The ROM 112 stores and maintains various types of programs executed by the CPU 111 or data needed for processing.

Furthermore, the RAM 113 is used mainly as a work area, such as temporarily storing intermediate results of processing, and is also used as a buffer memory or the like that stores and maintains acceleration data in the form of numeric values from the acceleration sensor 101 supplied via the A/D converter 102. The non-volatile memory 114 is a memory in which stored data is not deleted even when the memory is powered off, such as an EEPROM (Electrically Erasable and Programmable ROM) or a flash memory, and it stores and maintains data that is to be maintained even when power is turned off, such as parameters that have been set, added programs, and so forth.

Furthermore, the display unit 103 connected to the control unit 110 includes a display control circuit and is provided with a display element such as an LCD (Liquid Crystal Display), an organic EL (Electro Luminescence) display, or a CRT (Cathode-Ray Tube), and it displays a count value of the number of steps, various guidance information, and so forth according to control by the control unit 110. Specifically, in response to supply of display data from the control unit 110, the display unit 103 forms video signals to be supplied to the display element from the display data, and supplies the video signals to the display element, whereby display information corresponding to the display data from the control unit 110 is displayed on a display screen of the display element.

Furthermore, the operation unit 104 is provided with a reset key, various function keys, and so forth, and it is capable of receiving input of an operation by a user and supplying an electric signal corresponding thereto. The control unit 110 is configured to be capable of controlling individual parts in response to the electric signal and executing processing in accordance with the instruction by the user.

Furthermore, in the pedometer 100 of this embodiment, the control unit 110 implements the functions of the vertical-component extracting unit 2, the high-band/low-band separating unit 3, the peak detection/determination processing unit 4, and the step-position analyzing unit 5 of the body-movement detecting apparatus shown in FIG. 1, and also implements the function of a step measuring unit that performs step measurement.

That is, on the basis of detection outputs from the acceleration sensor 101, as described using FIG. 1, the control unit 110 of the pedometer 100 of this embodiment performs extraction of a vertical component, separation of a high-band/low-band of the vertical component, detection of a peak-position candidate and identification of a peak-position candidate, and decision of a peak position by waveform matching, and measures the number of steps on the basis of the decided peak position.

Furthermore, on the basis of the decided peak position, it is configured to be capable of accurately grasping the action state of the user and accurately grasping body-movement pitch of walking, running, or the like, so that in a case where the action state of the user is "walking/running", it is possible to measure the number of steps of the user more accurately on the basis of the body-movement pitch.

Hereinafter, with reference to flowcharts in FIGS. 16 to 21, various processes executed mainly by the control unit 110 of the pedometer of this embodiment shown in FIG. 15 will be described in detail.

[Regarding Vertical-Component Extracting Process]

Figure 16:
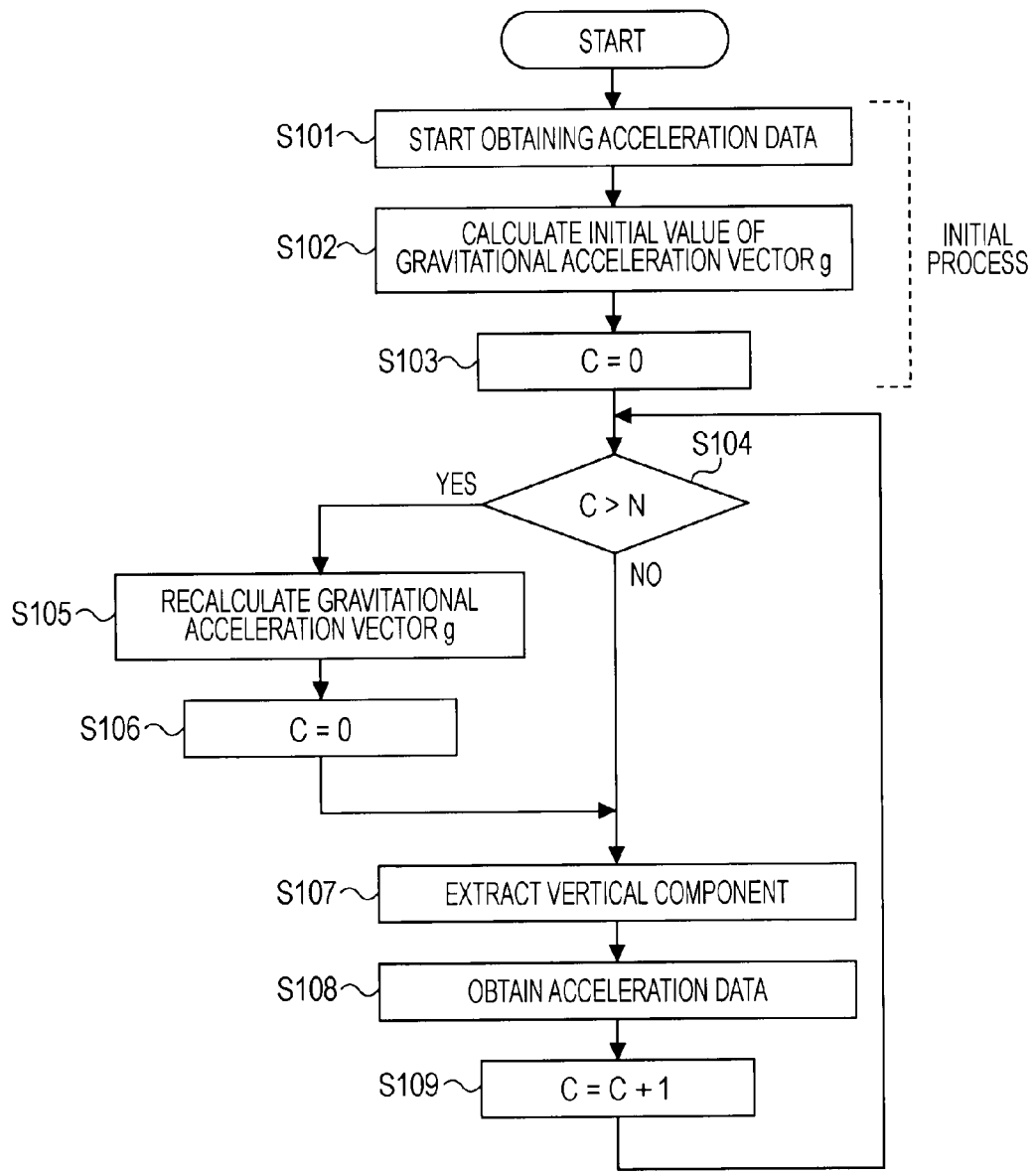
FIG. 16 is a flowchart for explaining a vertical-component extracting process.

FIG. 16 is a flowchart for explaining a vertical-component extracting process executed mainly by the control unit 110 of the pedometer 100 of this embodiment shown in FIG. 15. When the pedometer 100 of this embodiment is powered on and input of an instruction for executing measurement of the number of steps is accepted via the operation unit 104, the CPU 111 of the control unit 110 first executes a process shown in FIG. 16.

The control unit 110 starts a process of obtaining acceleration data (acceleration vector data) supplied via the A/D converter 102 and buffering the acceleration data in the RAM 113 (step S101), and calculates an initial value of the gravitational acceleration vector g using the obtained acceleration vector (step S102). Then, a sample counter c is reset (zero clear) (step S103). The process from step S101 to step S103 corresponds to what is called an initial process after the power-on.

Then, the control unit 110 determines whether the value of the sample counter c is greater than a predetermined value N (step S104). In this embodiment, in order to reduce the amount of calculation, recalculation of the gravitational acceleration vector g is performed at intervals of N (N is an integer greater than or equal to 1) samples.

When it is determined in the determination process of step S104 that the sample counter c is greater than the predefined value N, the control unit 110 performs the recalculation process of the gravitational acceleration vector g (step S105), and then sets a value 0 to the sample counter c (step S106). That is, the process of step S106 is a reset process of the sample counter c. Then, by using the gravitational acceleration vector g obtained by most recent recalculation and the acceleration vector an, a vertical component vn is obtained by calculation as described using FIG. 2 or FIG. 3 (step S107).

Furthermore, in a case where it is determined in step S104 that the value of the sample counter c is not greater than the value N, by using the initial value of the gravitational acceleration vector g calculated in step S102 and the most recent acceleration vector an, as described earlier, a vertical component vn is obtained by calculation as described using FIG. 2 or FIG. 3 (step S107).

Then, after the process of step S107, the control unit obtains the most recent acceleration data (step S108), adds 1 to the sample counter c (step S109), and repeats the process from step S104. The vertical component of the acceleration vector obtained in step S107 as above is used for the high-band/low-band separation process.

In this embodiment, the process of recalculating the gravitational acceleration vector 9 in step S105 and the process of calculating the initial value of the gravitational acceleration vector in step S102 are basically the same processes, and the gravitational acceleration vector g is calculated as an estimated value of gravitational acceleration by taking a moving average of data of the individual axes of the acceleration vector.

The processes executed in step S102 and step S105 will be described specifically. Here, a case will be considered where the current sample position is n1 and a gravitational acceleration is obtained from acceleration data of the past M samples.

In this case, in order to obtain a gravitational acceleration vector gx of the X axis, a sum is obtained by adding up acceleration data axn of the X axis in the individual samples from a sample that is M+1 samples before the current sample position to n1, and the sum is divided by the value M, whereby the gravitational acceleration vector gx of the X axis is obtained.

Similarly, in a case where a gravitational acceleration vector gy of the Y axis is to be obtained, a sum is obtained by adding up acceleration data ayn of the Y axis in the individual samples from the sample that is M+1 samples before the current sample position to n1, and dividing the sum by the value M, whereby the gravitational acceleration vector gy of the Y axis is obtained. Furthermore, in a case where a gravitational vector gz of the Z axis is to be obtained, a sum is obtained by adding up acceleration data azn of the Z axis in the individual samples from the sample that is M+1 samples before the current sample position to n1, and dividing the sum by the value M, whereby the gravitational acceleration vector gz of the Z axis is obtained.

In the case where a gravitational acceleration vector is calculated in the manner described above, it is desired that an average be taken using a sufficiently long segment so that acceleration components due to motion are averaged and canceled out. However, if the segment is too long, it fails to follow the tilt of the apparatus (it fails to correctly reflect the tilt of the apparatus), so that, for example, it is appropriate to set the period to be about several seconds.

Furthermore, in the process of extracting a vertical component in step S107, as described earlier, it is possible to obtain (extract) a vertical component vn on the basis of the most recent acceleration vector an and the gravitational vector g by equation (1-3) shown in FIG. 2 or equation (2-3) shown in FIG. 3.

As described above, the control unit 110 implements the function as the vertical-component extracting unit 2 by executing the process shown in FIG. 16.

Note that although estimation of the gravitational acceleration is performed at intervals of N samples in order to reduce the amount of calculation in the pedometer 100 of this embodiment as shown in FIG. 16, there is no limitation thereto. Estimation of the gravitational acceleration may be performed for every sample. The calculation process for estimation of the gravitational acceleration is not limited to taking moving averages of data of the individual axes. For example, the least square method or the like may be used.

[Regarding Process of High-Band/Low-Band Separation of Vertical Component]

Then, the vertical component of the acceleration vector extracted by the process shown in FIG. 16 is separated into a high-band component and a low-band component. In doing this, as described earlier, for example, by extracting, as the low-band component, components in a band of 2 Hz to 4 Hz, which includes main components of acceleration attributable to walking or running, and by extracting, as the high-band component, components in a band higher than 4 Hz, it is possible to separate the vertical component into a high-band component of a predetermined band and a low-band component of a predetermined band.

In the vertical component $x(n)$ extracted by the process shown in FIG. 16, peaks corresponding to up and down movements involved in walking exercise of the user occur. Particularly, in the low-band component $xl(n)$ of the vertical component $x(n)$, peaks corresponding to up and down movements involved in walking exercise of the user occur prominently. Thus, a peak-position candidate is detected on the basis of the low-band component $xl(n)$ obtained by separating the vertical component $x(n)$, and a peak-position candidate is identified on the basis of a ratio between energy of the low-band component $xl(n)$ and energy of the high-band component $xh(n)$.

[Regarding Process of Detecting and Identifying Peak-Position Candidate]

Figure 17:
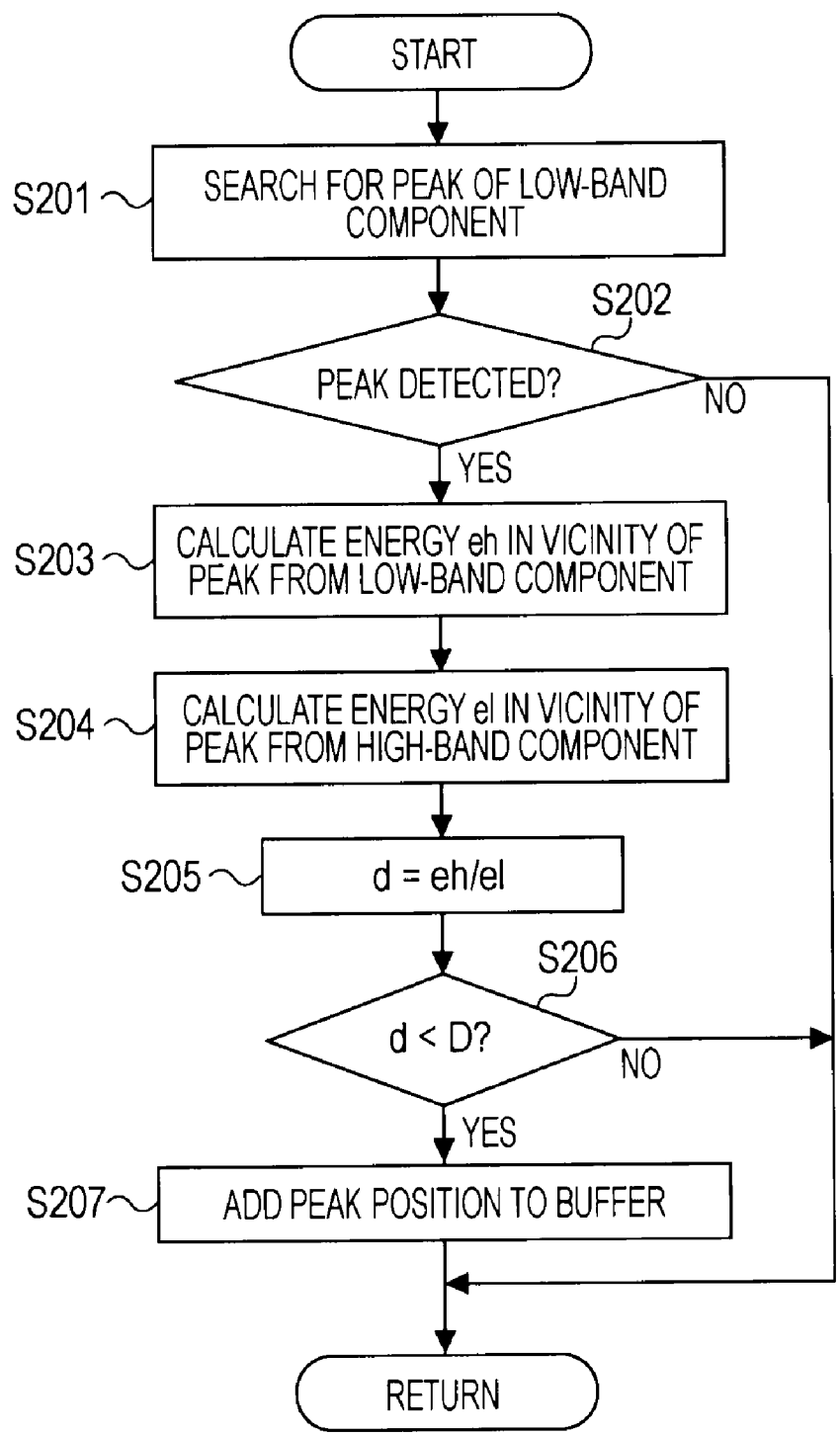
FIG. 17 is a flowchart for explaining a process of detecting and identifying a peak-position candidate.

FIG. 17 is a flowchart for explaining a process of detecting and identifying a peak-position candidate, executed mainly by the control unit 110 of the pedometer 100 of this embodiment shown in FIG. 15. The process shown in FIG. 17 is executed, for example, for each sampling, on the basis of the low-band component $xl(n)$ and the high-band component $xh(n)$ obtained by separating the vertical component $x(n)$ extracted by the vertical-component extracting process described using FIG. 16.

First, as described earlier, the control unit 110 executes a process of searching for (detecting) a peak-position candidate on the basis of the low-band component $xl(n)$ separated from the vertical component $x(n)$ (step S201). Specifically, regarding the low-band component $xl(n)$, for example, for each sampling, the most recently obtained low-band component data and the immediately preceding low-band component data are compared, and in a case where the immediately preceding low-band component data is larger and the immediately preceding low-band component data is greater than or equal to a predetermined value, the immediately preceding low-band component data is detected as a candidate of a peak value, and the position of the peak value is detected as a peak-position candidate.

Then, the control unit 110 determines whether a peak-position candidate has been detected (step S202), and when it is determined that no candidate has been detected, the control unit 110 finishes the process shown in FIG. 17, and execute the process shown in FIG. 17 again at a next timing of sampling.

On the other hand, when it is determined in the determining process of step S202 that a peak-position candidate has been detected, the control unit 110, by using the low-band component $xl(n)$ in the vicinity of the peak-position candidates, calculates the energy el of the low-band component $xl(n)$ in a predetermined range including the peak-position candidate according to equation (5-2) in FIG. 9 (step S203). Furthermore, similarly, the control unit 110, by using the high-band component $xh(n)$ in the vicinity of the peak-position candidate, calculates the energy eh of the high-band component $xh(n)$ in the predetermined range including the peak-position candidate according to equation (5-1) in FIG. 9 (step S204).

Then, according to equation (5-3) in FIG. 9, the control unit 110 calculates an energy ratio d between the energy el of the low-band component $xl(n)$ calculated in step S203 and the energy eh of the high-band component $xh(n)$ calculated in step S204 (step S205), and determines whether the calculated energy ratio d is less than a predetermined threshold D (step S206).

In a case where it is determined in the determination process of step S206 that the energy ratio d is not less than the predetermined threshold D, i.e., that a large amount of noise exists in the high-band component $xh(n)$, since the possibility that the position detected as the peak-position candidate is incorrect detection is high, the detected peak-position candidate is not identified as a peak-position candidate, the process shown in FIG. 17 is finished, and the process shown in FIG. 17 is executed again at a next timing of sampling.

In a case where it is determined in the determination process of step S206 that the energy ratio d is less than the predetermined threshold D, i.e., that noise in the high-band component $xh(n)$ is small, since the reliability of the position detected as the peak-position candidate is high as a peak position, the detected peak-position candidate is identified as a peak-position candidate, and the peak-position candidate is recorded, for example, in a peak-position recording buffer, such as the RAM 113 (step S207). Then, the process shown in FIG. 17 is finished, and the process shown in FIG. 17 is executed again at a next timing of sampling.

As above, the control unit 110 of the pedometer 100 of this embodiment detects a peak-position candidate on the basis of the low-band component xl(n) obtained by band division of the vertical component x(n) extracted from the acceleration vector an, and furthermore, identifies, as a peak-position candidate, only a position that is reliable as a peak-position candidate on the basis of the energy el of the low-band component xl(n) and the energy eh of the high-band component xh(n) in the predetermined range including the position detected as the peak-position candidate.

Note that the process shown in FIG. 17 is an implementation of the peak detecting function (the function of detecting and identifying a peak-position candidate) among the functions of the peak detection/determination processing unit 20 implemented by the control unit 110.

[Regarding Process of Waveform Matching and Number-of-Steps Counting]

Figure 18:
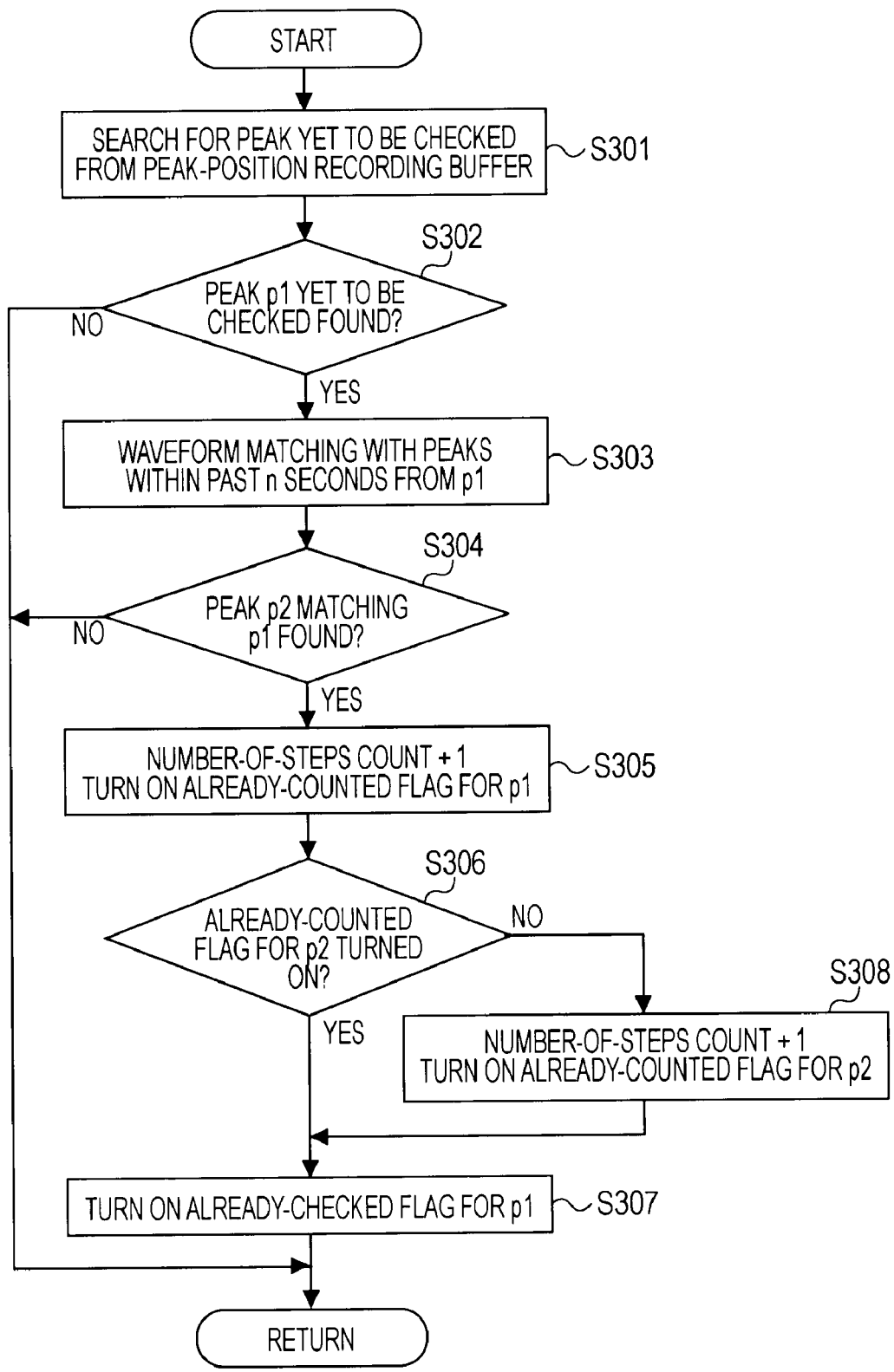
FIG. 18 is a flowchart for explaining a process of deciding a peak position from positions identified as peak-position candidates and counting the number of steps of the user on the basis of the peak position.

FIG. 18 is a flowchart for explaining a process of determining peak positions from positions identified as peak-position candidates and counting the number of steps of the user on the basis of the peak positions, which is a process executed mainly by the control unit 110 of the pedometer 100 of this embodiment shown in FIG. 15.

In the process shown in FIG. 18, on the basis of the peak-position candidates identified by the process shown in FIG. 17, waveform matching is performed between predetermined segments including peak-position candidates to determine true peak positions, and the determined peak positions are counted, thereby counting the number of steps of the user accurately.

The peak-position candidates identified by the process shown in FIG. 18 are stored in the peak-position recording buffer, for example, the RAM 113 or the like, by the process of step S207 in the process shown in FIG. 17. Thus, the control unit 110 finds (searches for) a peak-position candidate yet to be checked from the peak-position recording buffer (step S301). Whether a peak-position candidate is yet to be checked can be determined according to whether an already-checked flag set for each identified peak-position candidate is ON/OFF as will be described later. Usually, the most recently recorded peak-position candidate becomes a peak-position candidate yet to be checked.

Then, the control unit 110 determines whether a peak-position candidate p1 yet to be checked has been found in the process of step S301 (step S302). When it is determined in the determination process of step S302 that the peak-position candidate p1 yet to be checked has been found, a matching process is performed between a waveform in a predetermined range including the peak-position candidate p1 and a waveform in a predetermined range including another peak-position candidate in a range of the past N seconds from the peak-position candidate p1 (step S303).

Note that in the process of step S303, although it depends on the sampling frequency, matching with waveforms in one or more predetermined ranges is performed. Furthermore, regarding waveforms used for matching, it is performed on the basis of waveforms of the low-band component xl(n). Obviously, as waveforms for comparison, waveforms of the vertical component x(n) may be used.

Then, on the basis of the process of step S303, the control unit 110 determines whether a past peak-position candidate p2 matching the peak-position candidate p1 yet to be checked has been found (step S304). That is, in the determination process of step S304, it is determined whether a waveform in a predetermined range including a past peak-position candidate having a high degree of similarity with the waveform of the predetermined range including the peak-position candidate p1 yet to be checked has been found.

When it is determined in the determination process of step S304 that the past peak-position candidate p2 matching the peak-position candidate p1 yet to be checked has been found, the peak-position candidate p1 yet to be checked is determined as a peak position and "1" is added to the number-of-steps count, and the already-counted flag for the peak-position candidate p1 yet to be checked is turned on (step S305).

Furthermore, it is determined whether the already-counted flag of the past peak-position candidate p2, currently found as a match, is ON (step S306). In a case where the already-counted flag of the past peak-position candidate p2 is ON, the already-checked flag for the peak-position candidate p1 yet to be checked is turned on (step S307), the process shown in FIG. 18 is finished, and a next timing of execution is waited for.

On the other hand, when it is determined in the determination process of step S306 that the already-counted flag of the past peak-position candidate p2 is not ON, regarding the past peak-position candidate p2, although no matching peak exists before, since it newly matches the peak-position candidate p1, the past peak-position candidate p2 is also determined as a peak position and "1" is added to the number-of-steps count, and the already-counted flag for the past peak-position candidate p2 is turned on (step S308). Proceeding to the process of step S307, the already-checked flag for the peak-position candidate p1 yet to be checked is turned on (step S307), the process shown in FIG. 18 is finished, and a next timing of execution is waited for.

Furthermore, in the case where it is determined in the determination process of step S302 that the peak-position candidate p1 yet to be checked is not found and in the case where it is determined in the determination process of step S304 that the past peak-position candidate p2 matching the peak-position candidate p1 yet to be checked is not found, the process shown in FIG. 18 is finished, and a next timing of execution is waited for.

As above, after identifying peak-position candidates by the process described using FIG. 17, peak positions are decided and the decided peak positions are counted by the process shown in FIG. 18, so that it is possible to accurately count the number of steps corresponding to walking or running by the user.

Note that although the number of steps corresponding to walking or running of the user is accurately counted here by counting the decided peak positions by the process of FIG. 18, as long as an intended precision can be achieved, the number of steps corresponding to walking or running by the user may be counted by counting the number of peak-position candidates identified by the process shown in FIG. 17.

Note that the process shown in FIG. 18 implements the function of deciding a peak position among the functions of the peak detection/determination processing unit 4 implemented by the control unit 110, and also implements the function of measurement of the number of steps as a pedometer.

[Process for Preventing Counting Miss at the Beginning]

By the way, in the case of the process shown in FIG. 18, in a case where no peak exists in the past N seconds, as when walking is started from a stationary state, a counting miss occurs. Thus, it is possible to prevent a counting miss by adding a process of obtaining matching from a past peak to a current peak as in FIG. 19.

Figure 19:
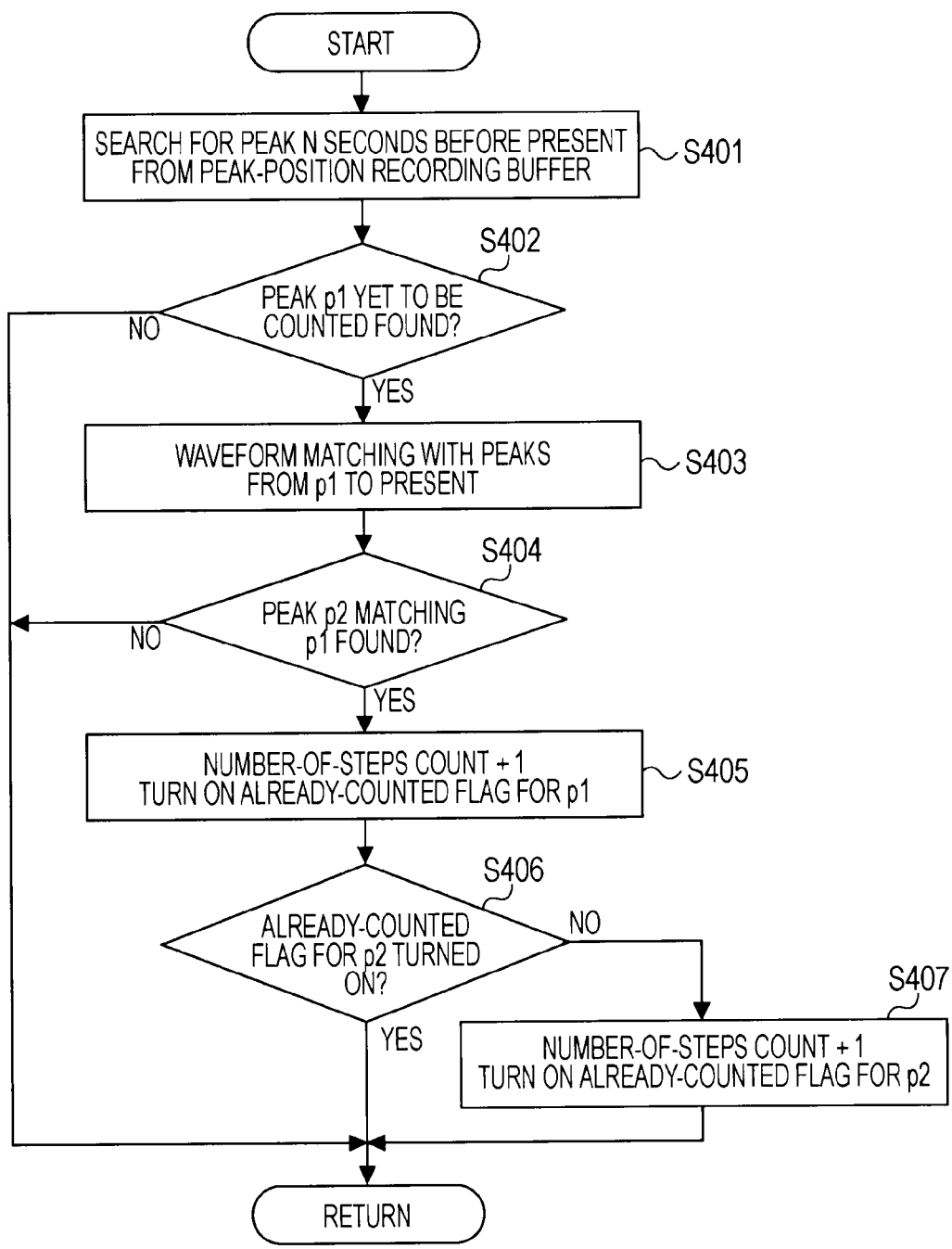
FIG. 19 is a flowchart for explaining a process of preventing a count miss mainly in the vicinity of the beginning.

That is, in a case where a counting miss of the number of steps immediately after the start of action (exercise) of the user is to be prevented, the process shown in FIG. 19 is added before or after the process shown in FIG. 18. In this case, the control unit 110 finds (searches for) a peak-position candidate p1 that is a peak-position candidate N seconds before the present and that is yet to be counted from the peak-position recording buffer (step S401).

The process of step S401 is a process of finding a past peak-position candidate that is yet to be counted. To put it shortly, it is a process of searching for a peak-position candidate at the beginning. The control unit 110 determines whether a peak-position candidate yet to be counted has been found (step S402).

When it is determined in the determination process of step S402 that a peak-position candidate p1 yet to be counted has been found, considering as a subject a range from the peak-position candidate p1 yet to be counted to the present, matching is performed between a waveform in the predetermined range including the peak-position candidate p1 yet to be counted and a waveform in the predetermined range including a peak-position candidate existing in the range from the peak-position candidate p1 yet to be counted to the present (step S403).

As opposed to the process in step S303 shown in FIG. 18, which is a waveform matching process in the direction from the present to the past, the process in step S403 is a waveform matching process in the direction from the past to the present.

Then, on the basis of the process in step S403, the control unit 110 determines whether a peak-position candidate p2 in the present direction matching the peak-position candidate p1 yet to be checked has been found (step S404). That is, in the determination process of step S404, it is determined whether a waveform in the predetermined range including a peak-position candidate having a high degree of similarity with the waveform in the predetermined range including the peak-position candidate p1 yet to be counted has been found in the present direction (the direction of elapse of time).

When it is determined in the determination process of step S404 that a peak-position candidate p2 in the present direction matching the peak-position candidate p1 yet to be checked has been found, "1" is added to the number-of-steps count, and the already-counted flag of the peak-position candidate p1 yet to be checked is turned on (step S405).

Thus, in a case where, for a past peak-position candidate not determined as a peak position since no peak-position candidate exists in the past, a waveform having a high degree of similarity exists by comparison with a subsequent waveform, it is possible to determine the past peak-position candidate as a peak position and to count the peak position.

Furthermore, the control unit 110 determines whether the already-counted flag for the peak-position candidate p2 in the present direction is ON (step S406). When it is determined in the determination process of step S406 that the already-counted flag for the peak-position candidate p2 in the present direction is not ON, the peak-position candidate p2 in the present direction is also determined as a peak position, the value "1" is added to the number-of-steps count, and the already-counted flag for the peak-position candidate p2 in the present direction is turned on (step S407).

Then, in the case where it is determined in the determination process of step S406 that the already-counted flag for the peak-position candidate p2 in the present direction is ON or after the process of step S407, the control unit 110 finishes the process shown in FIG. 19, and waits for a next timing of execution.

By executing the process shown in FIG. 19 in addition to the process shown in FIG. 19, for example, regarding a waveform in the vicinity of the first peak, it is possible to obtain matching with a waveform in the vicinity of a temporally later (future) peak to determine whether it is truly a peak, and to count it when it is a peak.

[Body-Movement-Type Estimation Process and Number-of-Steps Counting Process]

As described above, by identifying peak-position candidates and counting the peak-position candidates, or by determining true peak positions from peak-position candidates and counting the peak positions, it is possible to measure the number of steps during exercise of the user, such as walking or running. However, there are cases where peaks for which matching is not obtained occur due to the effect of noise or the like.

Thus, in the pedometer 100 of this embodiment, by the function as the step-position analyzing unit 5 implemented by the control unit 110, it is also possible to accurately grasp the action state of the user (body-movement type corresponding to the action state), and, in a case where walking or running is being performed, to accurately count the number of steps of the user even in a period where a peak for which it is not possible to obtain matching exists.

Figure 20:
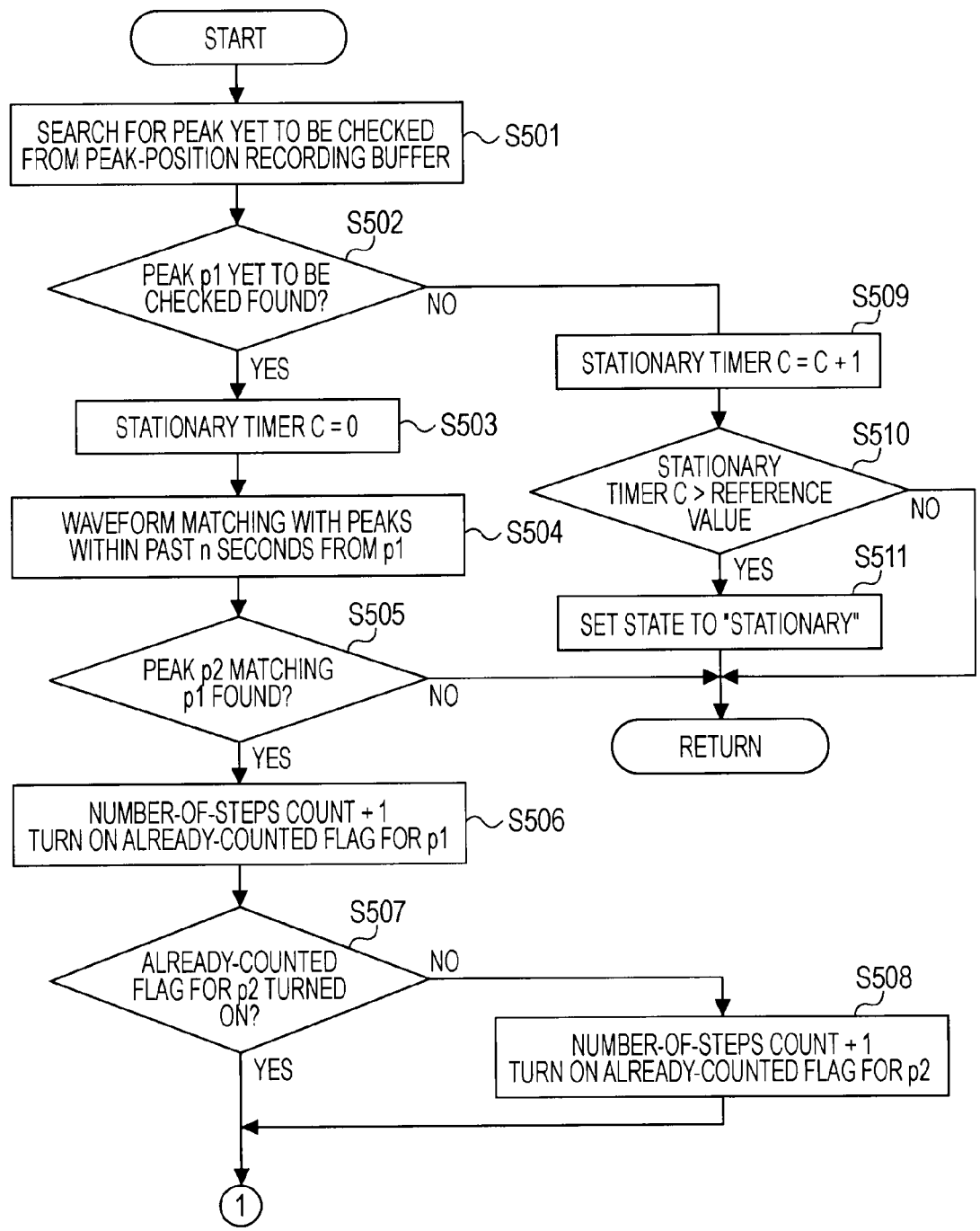
FIG. 20 is a flowchart for explaining a body-movement-type estimating process and a number-of-steps counting process.
Figure 21:
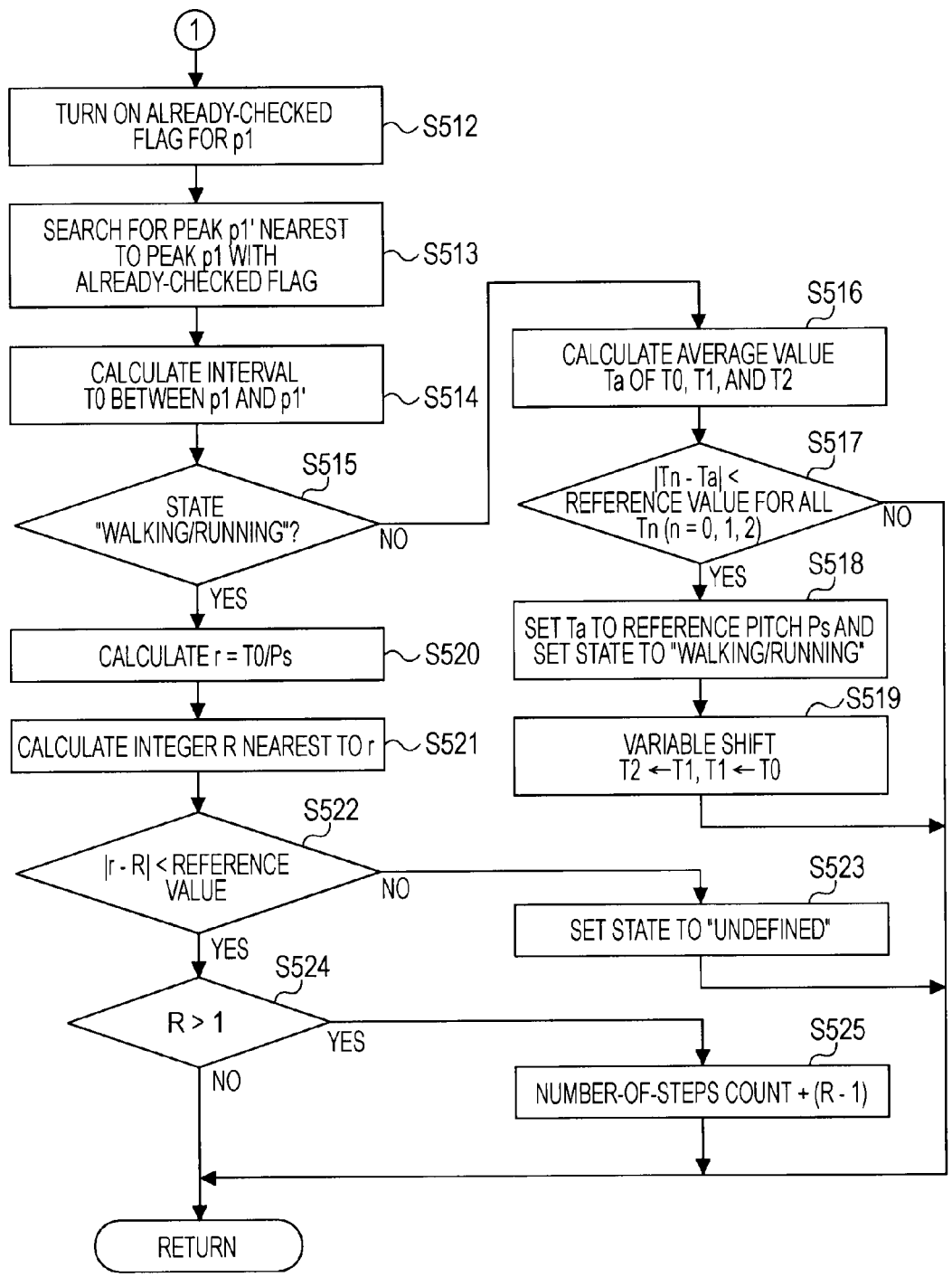
FIG. 21 is a flowchart subsequent to FIG. 20.

FIGS. 20 and 21 are flowcharts for explaining a body-movement-type estimation process and a number-of-steps counting process executed mainly by the control unit 110 of the pedometer 100 of this embodiment. As information of peak positions used in the processes shown in FIGS. 20 and 21, data of peak-position candidates identified by the process of FIG. 17 and recorded in the peak-position recording buffer is used, and a peak-position determining process by waveform matching, a body-movement-type estimating process, and a number-of-steps counting process are executed.

That is, subsequent to the processes in FIGS. 16 and 17, the processes shown in FIGS. 20 and 21 are executed. The processes in FIGS. 20 and 21 are implemented by the function of the peak detection/determination processing unit 4 and the function of the step-position analyzing unit 5.

Then, the control unit 110 finds (searches for) a peak-position candidate yet to be checked from the peak-position recording buffer, such as the RAM 113 (step S501). As will be described later, whether a peak-position candidate is yet to be checked can be discriminated on the basis of ON/OFF of the already-checked flag set for each identified peak-position candidate. Usually, a peak-position candidate recorded most recently becomes a peak-position candidate yet to be checked.

Then, the control unit 110 determines whether the peak-position candidate yet to be checked has been found in the process of step S501 (step S502). When it is determined in the determination process of step S502 that the peak-position candidate yet to be found has been found, the value "0 (zero)" is set to a stationary timer C (step S503). Then, the control unit 110 performs a matching process between a waveform in the predetermined range including the peak-position candidate p1 and a waveform in the predetermined range including another peak-position candidate in the range of the past N seconds from the peak-position candidate p1 (step S504).

Note that in the process of step S504, although it depends on the sampling frequency, matching is performed with waveforms in one or more past predetermined ranges. Furthermore, regarding waveforms used for matching, it can be performed on the basis of waveforms of the low-band component xl(n). Obviously, as waveforms used for comparison, waveforms of the vertical component x(n) may be used.

Then, on the basis of the process in step S504, the control unit 110 determines whether a past peak-position candidate p2 matching the peak-position candidate p1 yet to be checked has been found (step S505). That is, in the determination process of step S505, it is determined whether a waveform in a predetermined range including a past peak-position candidate having a high degree of similarity with the waveform in the predetermined range including the peak-position candidate p1 yet to be checked has been found.

When it is determined in the determination process of step S505 that the past peak-position candidate p2 matching the peak-position candidate p1 yet to be checked has been found, the peak-position candidate p1 yet to be checked is determined as a peak position, the value "1", is added to the number-of-steps count, and the already-counted flag for the peak-position candidate p1 yet to be checked is turned on (step S506).

Then, it is determined whether the already-counted flag for the past peak-position candidate p2 currently found as a match is ON (step S507). In a case where it is determined in the determination process of step S507 that the already-counted flag for the past peak-position candidate p2 is ON, the procedure proceeds to the process shown in FIG. 21.

On the other hand, when it is determined in the determination process of step S507 that the already-counted flag for the past peak-position candidate p2 is not ON, regarding the past peak-position candidate p2, although no matching peak exists before, since it newly matches the peak-position candidate p1, the past peak-position candidate p2 is also determined as a peak position, the value "1" is added to the number-of-steps count, the already-counted flag for the past peak-position candidate p2 is turned on (step S508), and the procedure proceeds to the process in FIG. 21.

Furthermore, when it is determined in the determination process of step S502 shown in FIG. 20 that the peak-position candidate p1 yet to be checked has not been found, the value "1" is added to the stationary timer C (step S509), and it is determined whether the stationary timer C has become greater than the reference value (step S510).

When it is determined in the determination process of step S510 that the stationary timer C has become greater than the reference value, the action state of the user is set as the "stationary" state (step S511), the processes in FIGS. 20 and 21 are finished, and a next timing of execution is waited for. On the other hand, when it is determined in the determination process of step S510 that the stationary timer C has not become greater than the reference value, without doing anything, the processes shown in FIGS. 20 and 21 are finished, and a next timing of execution is waited for.

Then, in the case where it is determined in the determination process of step S507 that the already-counted flag for the past peak-position candidate p2 is ON as described above and after the process of step S508, the process shown in FIG. 21 is executed. In the process shown in FIG. 21, the control unit 110 first turns on the already-checked flag for the peak-position candidate p1 yet to be checked (step S512).

Then, the control unit 110 identifies a past peak position p1' nearest to the peak position p1 for which the already-checked flag has been turned on most recently by the process of step S512 (step S513), and calculates an interval T0 between the peak position p1 and the immediately adjacent peak position p1' (step S514). In the pedometer 100 of this embodiment, as described using FIG. 12, it is possible to maintain three peak positions T0, T1, and T2 defined individually between immediately adjacent four peak positions. Obviously, a larger number of peak intervals may be maintained and used.

Then, the control unit 110 determines whether the result of determination of the most recent action state of the user is [walking/running] state (step S515). When it is determined in the determination process of step S515 that the movement stat of the user is not the [walking/running] state, as described above, an average value Ta of the three intervals T0, T1, and T2 determined in accordance with the immediately adjacent four peak positions is calculated (step S516), values obtained by subtracting the average value Ta are obtained individually for all the peak intervals T0, T1, and T2, and it is determined whether the values obtained are less than the reference value for all the peak intervals (step S517).

The determination process of step S517 is a process of determining whether the peak intervals T0, T1, and T2 are substantially the same pitch so that walking or running, which is a periodic body movement, has come to be performed. When it is determined in the determination process of step S517 that each of the differences between the individual peak intervals T0, T1, and T2 is less than or equal to the reference value, the control unit 110 sets the average value Ta as the reference pitch Ps, and determines (identifies) the action state of the user as "walking/running" (step S518).

Then, the control unit 110 performs a process of shifting the peak intervals T0, T1, and T2 (step S519). That is, the peak interval T1 is shifted to the peak interval T2, and the peak interval T0 is shifted to the peak interval T1. Note that as for the peak interval T0, initialization may be performed.

After the process of step S519 and in the determination process of step S517, when it is determined in the determination process of step S517 that each of the differences between the individual peak intervals T0, T1, and T2 and the average value Ta is not less than or equal to the reference value, the control unit 110 finishes the processes shown in FIGS. 20 and 21, and waits for a next timing of execution.

Furthermore, when it is determined in the determination process of step S515 that the action state of the user is the [walking/running], the control unit 110 divides the most recent peak interval T0 by the reference pitch Ps to calculate a value r (step S520). The process of step S520 is a process in which a case is considered where what is supposed to be detected as a peak value is not detected as a peak value, and is a process of calculating a number with which the peak interval T0 detected most recently is multiplied to become the reference pitch Ps.

Then, an integer R nearest to the value r calculated in step S520 is calculated (step S521). For example, in a case where the value r is "0.1", "0.2", or the like, the integer R is "0", in a case where the value r is "0.9", "1.1", or the like, the integer R is "1", and if the value r is "1.9" or "2.1", the integer R is "2". Then, the control unit 110 determines whether the absolute value of a value obtained by subtracting the integer R from the value r is less than a predetermined reference value (step S522).

The determination process of step S522 is a process of determining whether the most recent peak interval T0 is an integer multiple of the reference pitch Ps. When it is determined in the determination process of step S522 that the absolute value of the value obtained by subtracting the integer R from the value r is not less than the predetermined reference value, it is determined that the most recent peak interval T0 is not an integer multiple of the reference pitch Ps, and it is determined (identified) that the action state of the user is the "undefined" state (step S523). Then, the control unit 110 finishes the processes shown in FIGS. 20 and 21, and waits for a next timing of execution.

On the other hand, when it is determined in the determination process of step S522 that the absolute value of the value obtained by subtracting the integer R from the value r is less than the predetermined reference value, it is determined that the most recent peak interval T0 is an integer multiple of the reference pitch Ps, and it is determined whether the integer R1 is greater than the value "1" (step S524). The determination process of step S524 is a process of determining whether the peak interval T0 is greater than or equal to twice the reference pitch Ps.

When it is determined in the determination process of step S524 that the integer R is not greater than 1, since the most recent peak interval T0 is not a segment greater than or equal to twice the reference pitch, the control unit 110 finishes the processes shown in FIGS. 20 and 21 without doing anything, and waits for a next timing of execution.

On the other hand, when it is determined in the determination process of step S524 that the integer R is greater than 1, since the most recent peak interval T0 is a segment greater than or equal to twice the reference pitch, the control unit 110 adds a value obtained by subtracting 1 from the integer R to the count number (step S525), finishes the processes shown in FIGS. 20 and 21, and waits for a next timing of execution.

As above, in a case where walking or running is being performed while accurately discriminating action states of the user by the processes shown in FIGS. 20 and 21, even in a period where a peak for which matching is not obtained exists, it is possible to count the number of steps of the user accurately. Furthermore, it is also possible to discriminate in real time four action states (body-movement types corresponding to action states) of the "stationary" state, the "undefined" state, the "walking" state, and the "running" state.

Note that in the processes described using FIGS. 20 and 21, when the most recent peak interval T0 is a segment that is an integer multiple of the reference pitch, the number of steps is measured in accordance with a peak position for which measurement failed. However, there is no limitation thereto. That is, when the most recent peak interval T0 is a segment that is an integer multiple of the reference pitch, considering the amplitude of the low-band component of the vertical component and also the amplitude of the vertical component itself in the segment, it may be discriminated whether a peak position reliably exists at the position of the integer multiple of the reference pitch.

Specifically, a reference value for the amplitude at the position of an integer multiple of the reference pitch is provided, and if the amplitude is greater than or equal to the reference value, it is recognized as a peak value and peak position, and if the amplitude is less than the reference value, it is not recognized as a peak value and peak position. Note that it is possible to set an appropriate value as the reference value by performing experiments.

[Application to an Acoustic Playing Apparatus]

Figure 22:
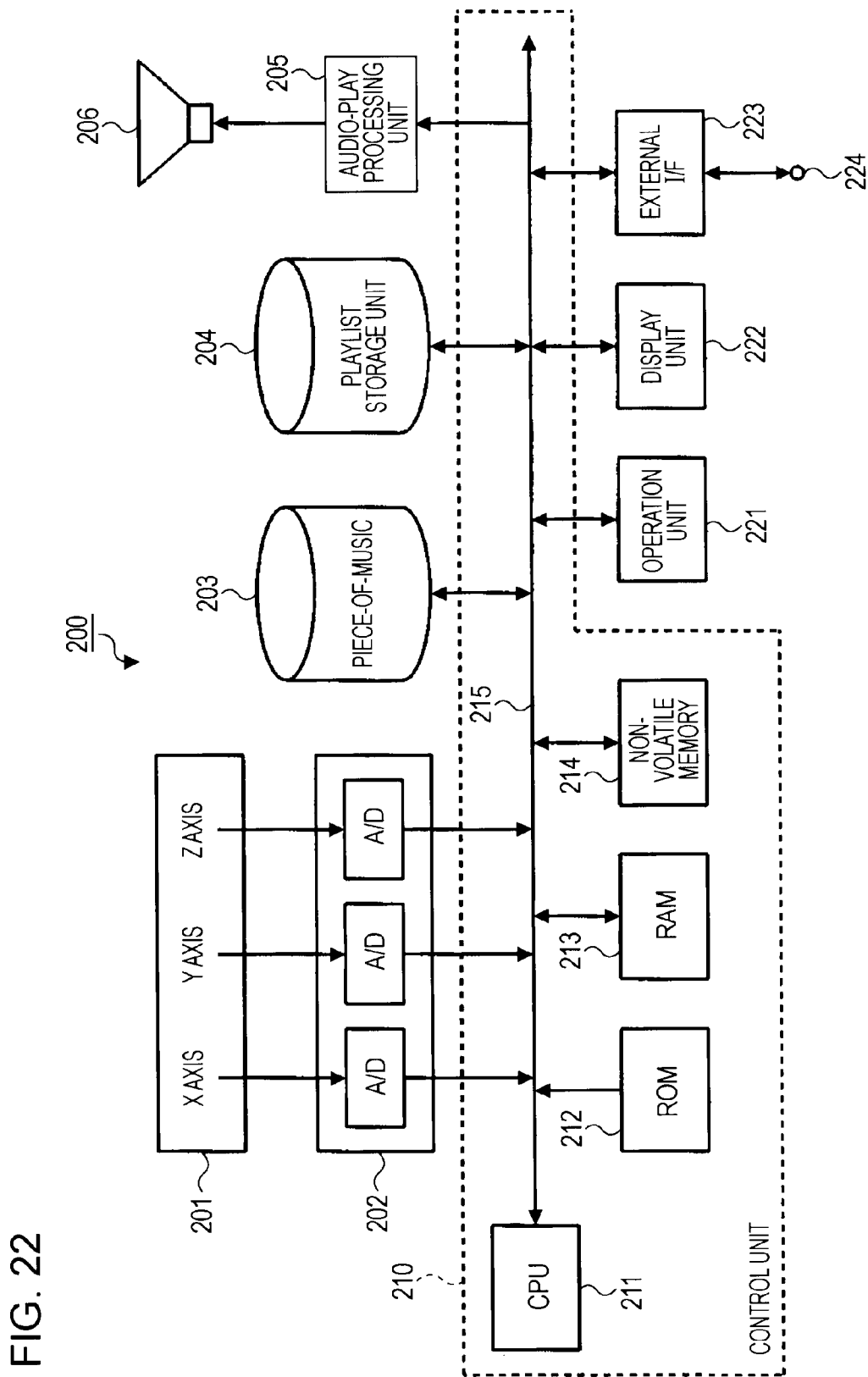
FIG. 22 is a block diagram for explaining an acoustic playing apparatus 200 to which an embodiment of this invention is applied.

Next, a case where an embodiment of an apparatus, method, and program of this invention is applied to an acoustic playing apparatus will be described. FIG. 22 is a block diagram for explaining an acoustic playing apparatus of this embodiment. As will be described later, the acoustic playing apparatus 200 of this embodiment is of a portable type that is configured to be capable of using a recording medium with a relatively large capacity for storing piece-of-music data (music data).

As the recording medium, use of various types of storage media is conceivable, such as a hard disk, a magneto-optical media such as an MD (Mini Disc (registered trademark)), an optical disc such as a CD or a DVD, a memory card, or a semiconductor memory. However, here, for simplicity of description, description will be given assuming that the recording medium for storing content data such as piece-of-music data is a hard disk.

As shown in FIG. 22, in the acoustic playing apparatus 200 of this embodiment, a three-axis acceleration sensor 201 is connected to a control unit 210 via an A/D converter 202, and as recording media with relatively large storage capacities, a piece-of-music database (hereinafter referred to as a piece-of-music DB) 203 and a playlist storage unit 204 are connected.

Furthermore, to the control unit 210, a speaker 206 is connected via an audio-playing processing unit 205, and an operation unit 221 and a display unit 222 as user interfaces are connected. Furthermore, it is configured with an input/output terminal 224 connected via an external interface (hereinafter referred to as an external I/F) 223.

Similarly to the acceleration sensor 101 of the pedometer 100 described earlier, as the three-axis acceleration sensor 201, either one formed by arranging one-axis acceleration sensors on three axes of an X axis, a Y axis, and a Z axis orthogonal to each other, or one formed by encapsulating acceleration sensors of orthogonal three axes in one package may be used. The individual detection outputs (analog outputs) of the X axis, Y axis, and Z axis from the three-axis acceleration sensor 201 are supplied to the A/D converter 202, where they are converted into digital data in a format in which processing by the control unit 210 is allowed, and the digital data is supplied to the control unit 210.

The control unit 210 controls individual parts of the acoustic playing apparatus 200 of this embodiment, and similarly to the control unit 110 of the pedometer 100 described earlier, it is configured as a microcomputer in which a CPU 211, a ROM 212, a RAM 213, and a non-volatile memory 214 are connected via a CPU bus 215.

Here, the CPU 211 executes various programs to form control signals supplied to individual parts, to perform various types of calculation, and so forth, and it serves as a main unit for processing or control in the control unit 210. The ROM 212 stores and maintains various types of programs executed by the CPU 211 or data needed for processing.

Furthermore, the PAM 213 is used mainly as a work area, such as temporarily storing intermediate results of processing, and is also used as a buffer memory or the like that stores and maintains acceleration data in the form of numeric values from the acceleration sensor 201 supplied via the A/D converter 202. The non-volatile memory 214 is a memory in which stored data is not deleted even when the memory is powered off, such as an EEPROM or a flash memory, and it stores and maintains data that is to be maintained even when power is turned off, such as parameters that have been set, added programs, and so forth.

Furthermore, as described earlier, each of the piece-of-music DB 203 and the playlist storage unit 204 is a hard disk. The piece-of-music DB stores and maintains data of a large number of pieces of music that can be played by the acoustic playing apparatus 200 of this embodiment, for example, as data compressed according to a predetermined data compression method.

Furthermore, the playlist storage unit 204 stores and maintains stationary-occasion playlists for instructing pieces of music to be played when the user is in the "stationary" state, walking-occasion playlists for instructing pieces of music to be played when the user is in the "walking" state, and running-occasion playlists for instructing pieces of music to be played when the user is in the "running" state.

That is, regarding playlists stored in the playlist storage unit 204, it is allowed to make distinction among stationary-occasion playlists, walking-occasion playlists, and running-occasion playlists, for example, by information such as playlist type attached to each playlist. Furthermore, a plurality of playlists exist individually as stationary-occasion playlists, walking-occasion playlists, and running-occasion playlists. Each playlist is formed by registering in advance, for example, in order of playing, piece-of-music IDs (piece-of-music identifiers) such as file names identifying one or more pieces of music to be played.

Note that although the piece-of-music DB 203 and the playlist storage unit 204 are shown separately in FIG. 22 in order to clarify the configuration, obviously, there are cases where these are formed on the same hard disk.

The audio-playing processing unit 205 receives supply of piece-of-music data read from the piece-of-music DB 203 by the control unit 210, executes a decompression process on the piece-of-music data to restore original piece-of-music data before data compression, forms analog audio signals in a format supplied to the speaker 206 from the restored piece-of-music data, and supplies the analog audio signals to the speaker 206. Thus, sound corresponding to the piece-of-music data chosen to be played is output from the speaker 206.

Note that, although not shown, the audio-playing processing unit 205 of this embodiment is configured to be also connected to a headphone terminal. In a case where a headphone is connected to the headphone terminal, audio signals processed by the audio-playing processing unit 205 are supplied to the headphone connected to the headphone terminal via the headphone terminal instead of the speaker 206, so that it is allowed to listen to the played sound via the headphone.

Furthermore, the operation unit 221 is provided with a play key, a stop key, a fast-forward key, a fast-rewind key, and various other function keys or the like, and it is capable of accepting input of operations by the user and supplying electric signals corresponding thereto to the control unit 210. In response to the electric signals, the control unit 210 is configured to be capable of controlling individual parts and executing processing in accordance with the user's instructions.

Furthermore, the display unit 222 includes a display control circuit and is provided with a display element such as an LCD (Liquid Crystal Display), an organic EL (Electro Luminescence) display, or a CRT (Cathode-Ray Tube), and it displays various guidance information and so forth according to control by the control unit 210. Specifically, in response to supply of display data from the control unit 210, the display unit 222 forms video signals to be supplied to the display element from the display data, and supplies the video signals to the display element, whereby display information corresponding to the display data from the control unit 210 is displayed on a display screen of the display element.

Furthermore, it is allowed to be connected to an external device, such as a personal computer, via the external I/F 223 and the input/output terminal 224. Furthermore, it is allowed to receive supply of piece-of-music data or a playlist from the external device via the input/output terminal 224 and the external I/F 223, and to store the piece-of-music data in the piece-of-music DB 203 while storing the playlist in the playlist storage unit 204.

Conversely, by the control of the control unit 210, it is also allowed to output piece-of-music data stored in the piece-of-music DB 203 to the external device via the control unit 210, the external I/F 223, and the input/output terminal 224, and to form a backup on a recording medium of the external device, or to similarly create a backup of a playlist stored and maintained in the playlist storage unit 204 on a recording medium of the external device.

Furthermore, by displaying a synopsis list of piece-of-music data stored in the piece-of-music DB 203 on the display unit 222, and selecting intended piece-of-music data via the operation unit 221 and inputting distinction among a stationary-occasion playlist, a walking-occasion playlist, and a running-occasion playlist, it is also possible to create a playlist on the acoustic playing apparatus 200 of this embodiment.

Furthermore, in the acoustic playing apparatus 200 of this embodiment, piece-of-music data selected via the operation unit 221 is read from the piece-of-music DB 203 by the control unit 210, and it is supplied to the audio-playing processing unit 205. Accordingly, it becomes possible to play a piece of music instructed from the user via the operation unit 221 so that the piece of music can be listened to.

Furthermore, in a case where a playlist to be used is instructed via the operation unit, piece-of-music data is read from the piece-of-music DB 203 by the control unit 210 according to the playlist instructed and is supplied to the audio-playing processing unit 205, so that it is allowed to play a piece of music according to the playlist.

Furthermore, in a case where a mode for automatically selecting a playlist is selected, it is also allowed to select an appropriate playlist in accordance with an action state of the user. In the acoustic playing apparatus 200 of this embodiment, the control unit 210 implements the functions as the vertical-component extracting unit 2, the high-band/low-band separating unit 3, the peak detection/determination processing unit 4, and the step-position analyzing unit 5 in the body-movement detecting apparatus shown in FIG. 1, and accurately grasps the action pitch (action tempo) of the user, so that it is possible to automatically select an appropriate playlist from stationary-occasion playlists, walking-occasion playlists, and running-occasion playlists in accordance with the action state of the user.

That is, the control unit 210 of the acoustic playing apparatus 200 of this embodiment has a function of executing processes such as extraction of a vertical component, separation of the vertical component into high-band/low-band, detection of a peak-position candidate and identification of a peak-position candidate, and decision of a peak position by waveform matching, on the basis of detection outputs from the acceleration sensor 201, as described using FIG. 1.

Furthermore, on the basis of the decided peak position, it is allowed to accurately grasp the action state of the user and to accurately grasp a body-movement pitch of walking, running, or the like, so that, by also taking the body-movement pitch into consideration, an appropriate playlist can be selected automatically in accordance with the action state of the user and a piece of music can be played using the selected playlist.

Figure 23:
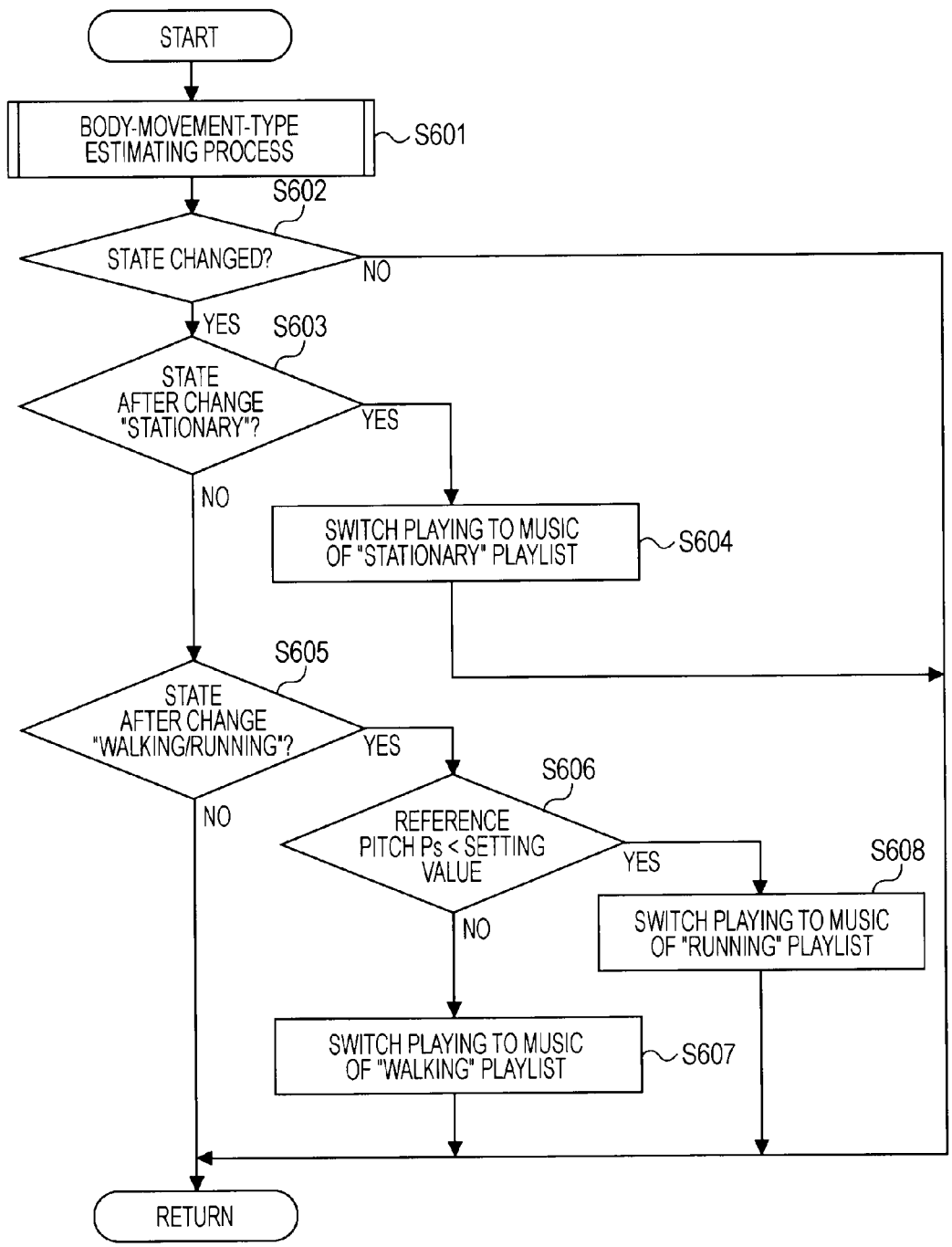
FIG. 23 is a flowchart for explaining a process in a case where an appropriate playlist is selected in accordance with an action state of the user.

Hereinafter, with reference to a flowchart in FIG. 23, a process in a case where an appropriate playlist is selected in accordance with the action state of the user in a case where a mode for automatically selecting a playlist in the acoustic playing apparatus of this embodiment will be described. FIG. 23 is a flowchart for explaining a process in a case where an appropriate playlist is selected in accordance with the action state of the user in the acoustic playing apparatus of this embodiment.

The process shown in FIG. 23 is executed mainly by the control unit 210 of the acoustic playing apparatus 200 of this embodiment. First, similarly to the case of the control unit 110 of the pedometer 100 shown in FIG. 15, the control unit 210 executes a body-movement-type estimating process (step S601). The process of step S601 is a process in which (1) as described using FIG. 16, a vertical component is extracted from an acceleration vector from the three-axis acceleration sensor 201, (2) the extracted vertical component is separated into a high-band component and a low-band component, (3) by using these components, as described using FIG. 17, peak-position candidates are identified, and (4) by using information of the identified peak-position candidates, the processes shown in FIGS. 20 and 21 are executed to grasp the action state and the action pitch of the user.

Note that in the processes shown in FIGS. 20 and 21, it is not necessary to execute a process of counting the number of steps. It is not necessary to execute the process of steps S506 to S508 and the process of step S525.

Then, the control unit 210 determines whether the action state of the user has changed (step S602). In the determination process, for example, as results of determination of the action state, the result of a previous determination and the result of a current determination are maintained, so that it is possible to determine that the action state has changed in a case where these results are different.

When it is determined in the determination process of step S602 that the action state has not changed, the process shown in FIG. 23 is finished, and a next timing of execution is waited for. When it is determined in the determination process of step S602 that the action state has changed, it is determined whether the state after the change, i.e., the result of the current determination, is the "stationary" state (step S603).

If it is determined in the determination process of step S603 that the result of the current determination is the "stationary" state, a stationary-occasion playlist stored in the playlist storage unit 204 is used, and a piece of music (music) is played according to the stationary-occasion playlist (step S604). Then, the process shown in FIG. 23 is finished, and a next timing of execution is waited for.

On the other hand, when it is determined in the determination process of step S603 that the result of the current determination is not the "stationary" state, it is determined whether the result of the current determination is the "walking/running" state (step S605). When it is determined in the determination process of step S605 that the result is the "walking/running" state, it is determined whether the reference pitch Ps obtained by the processes in FIGS. 20 and 21, which is the process of step S601, is less than a predefined value (step S606).

The predefined value used in the determination process of step S606 is a value for determining whether the action state of the user is walking or running. In a case where the reference pitch Ps is not less than the predefined value, it is possible to determine that the reference pitch is not yet sufficiently fast and that the state is the walking state. On the other hand, in a case where the reference pitch is less than the predefined value, it is possible to determine that the reference pitch is sufficiently fast and that the state is the running state.

Thus, when it is determined in the determination process of step S606 that the reference pitch PS is not less than the predefined value, the action state of the user is determined as the "walking" state, a walking-occasion playlist stored in the playlist storage unit 204 is used, and a piece of music (music) is played according to the walking-occasion playlist (step S607). Then, the control unit 210 finishes the process shown in FIG. 23, and waits for a next timing of execution.

On the other hand, when it is determined in the determination process of step S606 that the reference pitch PS is less than the predefined value, the action state of the user is determined as the "running" state, a running-occasion playlist stored in the playlist storage unit 204 is used, and a piece of music (music) is played according to the running-occasion playlist (step S608). Then, the control unit 210 finishes the process shown in FIG. 23, and waits for a next timing of execution.

As above, the acoustic playing apparatus 200 of this embodiment is configured to appropriately determine the action state of the user and to automatically switch to a playlist in accordance with the action state of the user, so that it is possible to play a piece of music in accordance with body movement of the user.

Note that as described earlier, there are cases where a plurality of playlists are prepared individually as stationary-occasion playlists, walking-occasion playlists, and running-occasion playlists. In such a case, the order of use may be defined in advance so that the playlists are used according to the order, or the frequencies of use of the individual playlists may be stored and a playlist with a low frequency of use may be used, or conversely, a playlist with a high frequency of use may be used. Alternatively, the user may specify in advance playlists to be used individually regarding stationary-occasion playlists, walking-occasion playlists, and running-occasion playlists.

Furthermore, also in the pedometer 100 described earlier, by executing the process in FIG. 19 prior to the processes in FIGS. 20 and 21, it is possible to measure the number of steps accurately from the beginning of the process of measuring the number of steps.

Furthermore, it has been described that the three-axis acceleration sensors 101 and 201 are used in the pedometer 100 and the acoustic playing apparatus 200 described above. However, there is no limitation thereto. A one-axis acceleration sensor may be used, or a two-axis acceleration sensor may be used. However, in a case where a one-axis or two-axis acceleration sensor is used, the acceleration sensor must be arranged in such a direction that main components of body movement can be picked up as signals.

However, it is preferable to use a three-axis acceleration sensor since restrictions do not arise regarding the mounting position or mounting direction by using a three-axis acceleration sensor and, as described earlier, by executing processes such as extraction of a vertical component and consideration of an energy ratio between a high-band component and a low-band component.

Furthermore, although a three-axis acceleration sensor is used and a vertical component is extracted from a three-axis acceleration vector in the embodiments described above, there is no limitation thereto. For example, a signal of an axis for which the signal intensity is strongest among the three axes may be regarded and selected as a vertical component.

Furthermore, although a pitch period of body movement is obtained by detecting peak positions of a vertical component of an acceleration vector in the pedometer 100 and the acoustic playing apparatus 200 described above, there is no limitation thereto. As means for identifying peak positions (step positions), such a mechanism may be provided that a switch is provided on the bottom of shoes and the contact of the switch is closed by stepping of a foot during walking or running, or means for detecting stepping may be provided by providing a distortion gauge on the bottom of shoes.

Furthermore, since it is possible to accurately measure the body-movement pitch (walking tempo or running tempo) of the user in the acoustic playing apparatus 200 of the embodiment described above, by causing the control unit 210 to control the audio-playing processing unit 205, it becomes possible to control the playing tempo of a piece of music that is played in accordance with the body-movement tempo of the user.

By controlling the playing tempo of a piece of music that is played in accordance with the body-movement tempo of the user as described above, the user feels a sense of togetherness with the piece of music that is played, so that it becomes possible to efficiently perform an exercise such as walking or running or to continue it comfortably.

Furthermore, the body-movement detecting apparatus, body-movement detecting method, and body-movement detecting program of the embodiments described above can be applied to various types of electronic devices that must be used by detecting body movement of a user in the vertical direction, for example, training machines such as in-house running machines used in fitness clubs or the like, or acoustic playing apparatuses of the installed type, as well as pedometers and portable acoustic playing apparatuses.

Furthermore, FIGS. 16 to 21 and FIG. 23 are applications of methods and programs according to this invention, and it is possible to use methods according to this invention by executing processes according to the flowcharts shown in FIGS. 16 to 21 and FIG. 23, and it is possible to implement programs according to this invention by creating programs according to the flowcharts shown in FIGS. 16 to 21 and FIG. 23.

Furthermore, by defining processes in a control unit so that the functions of the individual parts shown in FIG. 1 are implemented, it is possible to implement methods according to this invention. Similarly, by creating programs to be executed by a control unit so that the functions of the individual parts shown in FIG. 1 are implemented, it is possible to implement programs according to this invention.

According to this invention, it is possible to remove noise and to accurately detect body movement of the user in the vertical direction. That is, it is possible to implement an apparatus, method, and program for detecting body movement that are robust against noise (unsusceptible to the effect of noise).

The invention claimed is:

1. A body-movement detecting apparatus comprising:
an acceleration sensor configured to be mounted on a body of a user;
vertical-component extracting means for extracting a vertical component of an acceleration from a detection output from the acceleration sensor;
separating means for performing component separation of the vertical component extracted by the vertical-component extracting means into a high-band component and a low-band component;
detecting means for detecting a peak-position candidate on the basis of the low-band component of the vertical component separated by the separating means;
identifying means for identifying the peak-position candidate detected by the detecting means as a peak-position candidate in a case where a ratio between energy of the low-band component and energy of the high-band component in a predetermined range including the peak-position candidate is less than a predetermined value; and
body-movement detecting means for detecting body movement of the user on the basis of the peak-position candidate identified by the identifying means, said body-movement detecting means counting a number of peak-position position candidates to determine a number of body movements of the user.

2. The body-movement detecting apparatus according to claim 1, further comprising:
deciding means for setting, for each peak-position candidate identified by the identifying means, a predetermined range including the peak-position candidate, performing matching with a waveform in another predetermined range using a waveform in each set predetermined range as a subject, and deciding the peak-position candidate included in the waveform used as the subject as a peak position in a case where a degree of similarity is high,
wherein the body-movement detecting means detects body movement of the user on the basis of the peak position decided by the deciding means.

3. The body-movement detecting apparatus according to claim 1, further comprising:
interval estimating means for estimating a step interval by performing analysis regarding a time-series pattern formed of a plurality of peak-position candidates identified by the identifying means or a time-series pattern formed of a plurality of peak positions decided by the deciding means; and
discriminating means for discriminating at least three states of "stationary", "walking/running", and "undefined" as action states of the user on the basis of the step interval estimated by the interval estimating means.

4. The body-movement detecting apparatus according to claim 3, wherein:
when the state is "undefined", which is different from the "stationary" state, where no peak position is detected at all, and in which the step interval is not regular, determining means is capable of changing the action state of the user from "undefined" to "walking/running" in a case where the step interval is estimated by the interval estimating means as being regular during a number of steps, and
reference-pitch calculating means is provided for calculating a reference pitch on the basis of the step interval estimated by the interval estimating means in a case where the action state of the user has been changed by the determining means from "undefined" to "walking/running".

5. The body-movement detecting apparatus according to claim 4, wherein:
the determining means compares a most recent step interval estimated by the interval estimating means with the reference pitch, and maintains the state of "walking/running" in a case where a difference thereof is within a preset error range or within a predetermined error range relative to an integer multiple of the reference pitch.

6. The body-movement detecting apparatus according to claim 4, further comprising:
counting means for counting steps of the user on the basis of the step interval estimated by the interval estimating means,
wherein the counting means performs interpolation of count on the basis of an integer multiple of the reference pitch of the step interval in a case where the action state of the user is discriminated as "walking/running" by the discriminating means.

7. The body-movement detecting apparatus according to claim 4, further comprising:
determining means for determining whether the action state of the user is "walking" or "running" on the basis of the step interval estimated by the interval estimating means in a case where the action state of the user is discriminated by the discriminating means as the state of "walking/running".

8. The body-movement detecting apparatus according to claim 1, further comprising:
determining means for determining whether the action state of the user is "walking" or "running" on the basis of a peak value of the low-band component obtained by the obtaining means and the step interval estimated by the interval estimating means in a case where the action state of the user is discriminated by the discriminating means as the state of "walking/running".

9. The body-movement detecting apparatus according to claim 3, further comprising:
piece-of-music playlist maintaining means for storing and maintaining one or more piece-of-music playlists formed in association with action states of the user; and
selecting means for selecting a piece-of-music playlist used to play a piece of music from the piece-of-music playlist maintaining means in accordance with an action state of the user discriminated by the discriminating means.

10. The body-movement detecting apparatus according to claim 1, further comprising:
playing means for piece-of-music data;
playing controlling means for controlling a playing rate of a piece of music by the playing means in accordance with a period of body movement of the user detected by the body-movement detecting means,
wherein the body-movement detecting apparatus has a function as a piece-of-music playing apparatus.

11. The body-movement detecting apparatus according to claim 1, wherein:
the acceleration sensor is of a multi-axis type, and
the vertical-component extracting means calculates a gravitational acceleration vector from an acceleration vector that is a detection output from the multi-axis acceleration sensor, and extracts a vertical component of an acceleration by performing calculation using the acceleration vector from the multi-axis acceleration sensor and the calculated gravitational acceleration vector.

12. A body-movement detecting method comprising:
a vertical-component extracting process of extracting a vertical component of an acceleration from a detection output of the acceleration sensor configured to be mounted on a body of a user;
a separating process of performing component separation of the vertical component extracted in the vertical-component extracting process into a high-band component and a low-band component;
a detecting process of detecting a peak-position candidate on the basis of the low-band component of the vertical component separated in the separating process;
an identifying process of identifying the peak-position candidate detected in the detecting process as a peak-position candidate in a case where a ratio between energy of the low-band component and energy of the high-band component in a predetermined range including the peak-position candidate is less than a predetermined value; and
a body-movement detecting process of detecting body movement of the user on the basis of the peak-position candidate identified in the identifying process, said body-movement detecting process counting a number of peak-position position candidates to determine a number of body movements of the user.

13. The body-movement detecting method according to claim 12, further comprising:
a deciding process of setting, for each peak-position candidate identified in the identifying process, a predetermined range including the peak-position candidate, performing matching with a waveform in another predetermined range using a waveform in each set predetermined range as a subject, and deciding the peak-position candidate included in the waveform used as the subject as a peak position in a case where a degree of similarity is high,
wherein, in the body-movement detecting process, body movement of the user is detected on the basis of the peak position decided in the deciding process.

14. The body-movement detecting method according to claim 12, further comprising:
an interval estimating process of estimating a process interval by performing analysis regarding a time-series pattern formed of a plurality of peak-position candidates identified in the identifying process or a time-series pattern formed of a plurality of peak positions decided in the deciding process; and
a discriminating process of discriminating at least three states of "stationary", "walking/running", and "undefined" as action states of the user on the basis of the process interval estimated in the interval estimating process.

15. The body-movement detecting method according to claim 12, wherein:
the acceleration sensor configured to be mounted on the body of the user is of a multi-axis type, and
in the vertical-component extracting process, a gravitational acceleration vector is calculated from an acceleration vector that is a detection output from the multi-axis acceleration sensor, and a vertical component of an acceleration is extracted by performing calculation using the acceleration vector from the multi-axis acceleration sensor and the calculated gravitational acceleration vector.

16. A non-transitory computer readable medium encoded with a body-movement detecting program causing a computer, the computer being mounted on a body-movement detecting apparatus that is provided with an acceleration sensor configured to be mounted on a body of a user and that detects body movement of the user by using a detection output from the acceleration sensor, to execute a method comprising:
a vertical-component extracting step of extracting a vertical component of an acceleration from the detection output of the acceleration sensor;
a separating step of performing component separation of the vertical component extracted in the vertical-component extracting step into a high-band component and a low-band component;
a detecting step of detecting a peak-position candidate on the basis of the low-band component of the vertical component separated in the separating step;
an identifying step of identifying the peak-position candidate detected in the detecting step as a peak-position candidate in a case where a ratio between energy of the low-band component and energy of the high-band component in a predetermined range including the peak-position candidate is less than a predetermined value; and
a body-movement detecting step of detecting body movement of the user on the basis of the peak-position candidate identified in the identifying step, said body-movement detecting step counting a number of peak-position position candidates to determine a number of body movements of the user.

17. The non-transitory computer readable medium according to claim 16, wherein the method further comprises:
a deciding step of setting, for each peak-position candidate identified in the identifying step, a predetermined range including the peak-position candidate, performing matching with a waveform in another predetermined range using a waveform in each set predetermined range as a subject, and deciding the peak-position candidate included in the waveform used as the subject as a peak position in a case where a degree of similarity is high, wherein, in the body-movement detecting step, body movement of the user is detected on the basis of the peak position decided in the deciding step.

18. The non-transitory computer readable medium according to claim 16, wherein the method further comprises:

an interval estimating step of estimating a step interval by performing analysis regarding a time-series pattern formed of a plurality of peak-position candidates identified in the identifying step or a time-series pattern formed of a plurality of peak positions decided in the deciding step; and a discriminating step of discriminating at least three states of "stationary", "walking/running", and "undefined" as action states of the user on the basis of the step interval estimated in the interval estimating step.

19. The non-transitory computer readable medium according to claim 16, wherein:

the acceleration sensor configured to be mounted on the body of the user is of a multi-axis type, and in the vertical-component extracting step, a gravitational acceleration vector is calculated from an acceleration vector that is a detection output from the multi-axis acceleration sensor, and a vertical component of an acceleration is extracted by performing calculation using the acceleration vector from the multi-axis acceleration sensor and the calculated gravitational acceleration vector.

20. A body-movement detecting apparatus comprising:

an acceleration sensor configured to be mounted on a body of a user;

a vertical-component extractor configured to extract a vertical component of an acceleration from a detection output from the acceleration sensor;

a separating unit configured to separate components of the vertical component extracted by the vertical-component extractor into a high-band component and a low-band component;

a detector configured to detect a peak-position candidate on the basis of the low-band component of the vertical component separated by the separating unit;

an identifying unit configured to identify the peak-position candidate detected by the detector as a peak-position candidate in a case where a ratio between energy of the low-band component and energy of the high-band component in a predetermined range including the peak-position candidate is less than a predetermined value; and a body movement detector configured to detect body movement of the user on the basis of the peak-position candidate identified by the identifying unit, said body-movement detector configured to count a number of peak-position position candidates to determine a number of body movements of the user.

* * * * *